United States Patent
Aissaoui et al.

(10) Patent No.: US 8,003,654 B2
(45) Date of Patent: Aug. 23, 2011

(54) N-GLYCINSULFONAMIDE DERIVATIVES AND USES AS OREXIN RECEPTOR ANTAGONISTS

(75) Inventors: Hamed Aissaoui, Pulversheim (FR); Christoph Boss, Allschwil (CH); Markus Gude, Allschwil (CH); Ralf Koberstein, Lorrach (DE); Thierry Sifferlen, Wentzwiller (FR); Cornelia Zumbrunn Acklin, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 237 days.

(21) Appl. No.: 12/296,842

(22) PCT Filed: Apr. 10, 2007

(86) PCT No.: PCT/IB2007/051280

§ 371 (c)(1), (2), (4) Date: Oct. 10, 2008

(87) PCT Pub. No.: WO2007/116374

PCT Pub. Date: Oct. 18, 2007

(65) Prior Publication Data

US 2009/0275588 A1  Nov. 5, 2009

(30) Foreign Application Priority Data

Apr. 11, 2006  (WO) ................. PCT/IB2006/051115

(51) Int. Cl.
*A61K 31/4965* (2006.01)

(52) U.S. Cl. .............. 514/255.06; 544/322; 544/336; 546/304; 548/136; 548/202; 548/214; 548/235; 548/247; 548/375.1

(58) Field of Classification Search ............ 514/255.06; 544/322, 336; 546/304; 548/136, 202, 214, 548/235, 247, 375.1
See application file for complete search history.

(56) References Cited

U.S. PATENT DOCUMENTS

| 7,279,578 B2 | 10/2007 | Aissaoui et al. | |
| 7,396,958 B2 * | 7/2008 | Courtemanche et al. | ....... 564/92 |
| 7,435,815 B2 | 10/2008 | Aissaoui et al. | |

FOREIGN PATENT DOCUMENTS

| WO | WO00/50391 | 8/2000 |
| WO | WO02/32864 | 4/2002 |
| WO | WO2004/033418 | 4/2004 |
| WO | WO2004/058702 | 7/2004 |
| WO | WO2005/118548 | 12/2005 |
| WO | WO2006/024779 | 3/2006 |

OTHER PUBLICATIONS

Ashimori et al., Novel 1,4-Dihydropyridine Calcium Antagonists. I. Synthesis and Hypotensive Activity of 4-(Substituted Pyridyl)-1,4-dihydropyridine Derivatives, Chem. Pharm. Bull., vol. 38, No. 9, 2446-2458 (1990).
Buttimore et al., Isothiazoles, Part II[1] Isothiazolealdehydes and Isothiazolyl Ketones, J. Amer. Chem. Soc., 2032-2039 (1963).
Buttimore et al., Isothiazoles, Part VIII[1] Reactions of 3-Bromomethylisothiazoles, J. Amer. Chem. Soc., 7274-7276 (1965).
Calderwood et al., Selective Tolyl Carbon Alkylation Mediated by Imidazoline-Directed Lithiation, Synth. Commun., vol. 34, No. 19, 3455-3464 (2004).
Chemelli et al., Narcolepsy in *orexin* Knockout Mice: Molecular Genetics of Sleep Regulation, Cell, vol. 98, 437-451 (Aug. 20, 1999).
Comins et al., Lithiation of Methoxypyridines Directed by α-Amino Alkoxides, J. Org. Chem., 55, 69-73 (1990).
Deshong et al., A General Method for the Synthesis of Tetramic Acid Derivatives, J. Org. Chem., 53, 1356-1364 (1988).
Eiermann et al., [2.2](2,6)- and [2,2](2,5)Pyrazinophanes: Synthesis and Molecular Structure, Chem. Ber., 123, 523-533 (1990).
Gibson (Editor), Pharmaceutical Preformulation and Formulation, IHS Health Group, Englewood CO, USA (2001).
Gould, Salt Selection for Bacis Drugs, International Journal of Pharmaceutics, 33, 201-217 (1986).
Hamilton et al., The Preparation of Aromatic Arsonic and Arsinic Acids by the Bart, Bechamp, and Rosenmund Reactions, Org. React., 2, 428 (1944).
Juanes et al., Synthesis of Macrobicyclic Ligands containing Pyrazole Subunits: the *N,N'*-Bibyrazolyl Cryptand, Chem. Soc. Chem. Commun., 24, 1765-1766 (1985).
Kemnitzer et al., Discovery of 4-Aryl-4*H*-chromenes as a New Series of Apoptosis Inducers Using a Cell- and Caspase-based High Throughput Screening Assay. 1. Structure-Activity Relationships of the 4-Aryl Group, J. Med. Chem., 47, 6299-6310 (2004).
Khanna et al., Selective Cyclooxygenase-2 Inhibitors: Heteroaryl Modified 1,2-Diarylimidazoles Are Potent, Orally Active Antiinflammatory Agents, J. Med. Chem. 43, 3168-3185 (2000).
Li et al., Synthesis and Biological Evaluation of *N*-Heterocylic Indolyl Glyoxylamides as Orally Active Anticancer Agents, J. Med. Chem., 46, 1706-1715 (2003).
Ma et al., Novel Chelating Agents for Potential Clinical Applications of Copper, Nuclear Medicine and Biology, 29, 91-105 (2002).
Newkome et al., α-Methyl Functionalization of Electron-Poor Hetercycles[1]: Free Radical Chlorination, Synthesis, 676-679 (1984).
Pattenden et al., Total Synthesis of (+)-phorboxazole A, a Potent Cytostatic Agent from the Sponge *Phrobas* sp., Org. & Biomolecular Chem., 1, 23, 4173-4208 (2003).
Russell et al., Discovery of Functionally Selective 7,8,9,10-Tetrahydro-7,10-ethano-1,2,4-triazolo[3,4-*a*]phthalizines as $GABA_A$ Receptor Agonists at the $\alpha_3$ Subunit, J. Med. Chem., 48, 1367-1383 (2005).
Sakurai et al., Orexins and Orexin Receptors: A Family of Hypothalamic Neuropeptides and G Protein-Coupled Receptor that Regulate Feeding Behavior, Cell, vol. 92, 573-585 (Feb. 20, 1998).

* cited by examiner

*Primary Examiner* — James O. Wilson
*Assistant Examiner* — Douglas M Willis
(74) *Attorney, Agent, or Firm* — Hoxie & Associates LLC

(57) ABSTRACT

The invention relates to novel sulfonamide compounds of the formula (I)

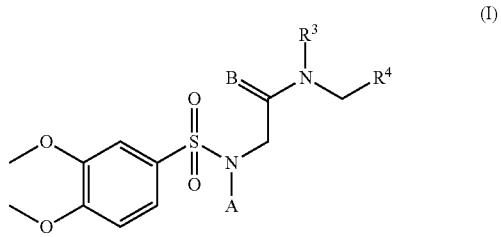

and their use as orexin receptor antagonists.

12 Claims, No Drawings

N-GLYCINSULFONAMIDE DERIVATIVES AND USES AS OREXIN RECEPTOR ANTAGONISTS

CROSS-REFERENCE TO RELATED APPLICATIONS

This application is a United States Application under 35 U.S.C. 371 claiming benefit of PCT Application No. PCT/IB2007/051280, filed on Apr. 10, 2007, which claims the benefit of PCT Application No. PCT/IB2006/051115, filed on Apr. 11, 2006, the contents of each of which are hereby incorporated by reference in their entirety.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION BY REFERENCE OF MATERIAL SUBMITTED ON A COMPACT DISC

Not Applicable.

BACKGROUND OF THE INVENTION

1. Field of the Invention

The present invention relates to novel sulfonamide compounds of formula (I) and their use as pharmaceuticals. The invention also concerns related aspects including processes for the preparation of the compounds, pharmaceutical compositions containing one or more compounds of formula (I), and especially their use as orexin receptor antagonists.

2. Description of Related Art

Orexins (orexin A or OX-A and orexin B or OX-B) are novel neuropeptides found in 1998 by two research groups, orexin A is a 33 amino acid peptide and orexin B is a 28 amino acid peptide (Sakurai T. et al., Cell, 1998, 92, 573-585). Orexins are produced in discrete neurons of the lateral hypothalamus and bind to the G-protein-coupled receptors ($OX_1$ and $OX_2$ receptors). The orexin-1 receptor ($OX_1$) is selective for OX-A, and the orexin-2 receptor ($OX_2$) is capable to bind OX-A as well as OX-B. Orexins are found to stimulate food consumption in rats suggesting a physiological role for these peptides as mediators in the central feedback mechanism that regulates feeding behaviour (Sakurai T. et al., Cell, 1998, 92, 573-585). On the other hand, it was also observed that orexins regulate states of sleep and wakefulness opening potentially novel therapeutic approaches to narcolepsy as well as insomnia and other sleep disorders (Chemelli R. M. et al., Cell, 1999, 98, 437-451).

Orexin receptors are found in the mammalian brain and may have numerous implications in pathologies such as dysthymic, mood, psychotic and anxiety disorders; diabetes and appetite, taste, eating, or drinking disorders; hypothalamic diseases; disturbed biological and circadian rhythms; sleep disturbances associated with diseases such as neurological disorders, neuropathic pain and restless leg syndrome; insomnias related to psychiatric disorders; sleep apnea; narcolepsy; idiopathic insomnias; parasomnias; benign prostatic hypertrophy; all dementias and cognitive dysfunctions in the healthy population and in psychiatric and neurologic disorders; and other diseases related to general orexin system dysfunctions.

The present invention provides N-glycinsulfonamide derivatives, which are non-peptide antagonists of human orexin receptors. These compounds are in particular of potential use in the treatment of e.g. eating disorders, drinking disorders, sleep disorders, or cognitive dysfunctions in psychiatric and neurologic disorders.

WO 00/50391 discloses certain sulfonamide derivatives as modulators of the production of amyloid β-protein. WO 02/32864 discloses certain sulfanilide derivatives useful in the treatment of diseases mediated by oxytocin and/or vasopressin.

WO 2004/033418 discloses sulfonylamino-acetic acid derivatives as selective $OX_2$ receptor antagonists. Recently sulfonamide derivatives as selective $OX_2$ receptor antagonists have been described in WO 2006/024779.

BRIEF SUMMARY OF THE INVENTION

Brief Description of the Several Views of the Drawings

Not Applicable.

A first aspect of the invention consists of a compound of the formula (I)

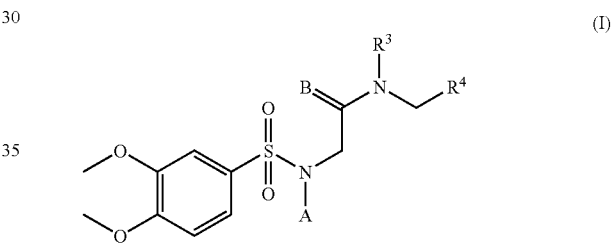

wherein
A represents

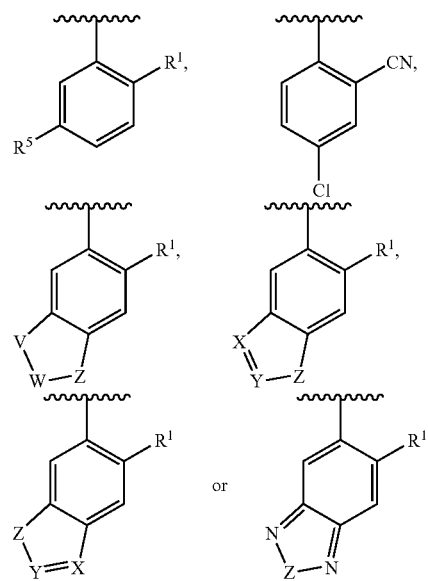

or

B represents O or S;
V represents —O—, —S—, —N(R²)— or —C(H)(R²)—;
W represents —C(H)(R²)—;
X represents =N— or =C(R²)—;
Y represents =N— or =C(R²)—;
Z represents —O—, —S—, —N(R²)—, or
R¹ represents halogen or cyano;
R² represents hydrogen or (C₁₋₄)alkyl;
R³ represents (C₁₋₄)alkyl, (C₃₋₆)cycloalkyl or hydroxy(C₁₋₄)alkyl;
R⁴ represents (C₁₋₄)alkyl or an unsubstituted or mono or di-substituted five or six-membered heteroaryl wherein the substituents are independently selected from the group consisting of halogen, (C₁₋₄)alkyl, (C₁₋₄)alkoxy, trifluoromethyl, difluoromethoxy and trifluoromethoxy;
R⁵ represents N(CH₃)₂, or isopropenyl.

Also part of the invention are compounds of the general formula (I) and pharmaceutically acceptable salts thereof.

The term "(C₁₋₄)alkyl", alone or in combination, means a straight-chain or branched-chain alkyl group with 1 to 4 carbon atoms. Examples of (C₁₋₄)alkyl groups are methyl, ethyl, propyl, isopropyl, n-butyl, isobutyl, sec.-butyl or tert.-butyl. Preferred are methyl and ethyl.

In case R² represents "(C₁₋₄)alkyl" the term means methyl and ethyl, preferably methyl.

In case R³ represents "(C₁₋₄)alkyl" the term means methyl and ethyl, preferably ethyl.

In case R⁴ represents "(C₁₋₄)alkyl" the term means methyl and ethyl, preferably methyl.

The term "hydroxy(C₁₋₄)alkyl", alone or in combination, means a group of the formula HO—(C₁₋₄)alkyl-, in which the term "(C₁₋₄)alkyl" has the previously given significance, such as methoxy, ethoxy, n-propoxy, isopropoxy, n-butoxy, isobutoxy, sec.-butoxy or tert.-butoxy.

Preferred are hydroxy-methyl and hydroxy-ethyl; more preferred hydroxy-ethyl.

The term "(C₁₋₄)alkoxy", alone or in combination, means a group of the formula (C₁₋₄)alkyl-O— in which the term "(C₁₋₄)alkyl" has the previously given significance, such as methoxy, ethoxy, n-propoxy, isopropoxy, n-butoxy, isobutoxy, sec.-butoxy or tert.-butoxy.

Preferred are methoxy and ethoxy; more preferred methoxy.

The term "(C₃₋₆)cycloalkyl", alone or in combination, means a cycloalkyl ring with 3 to 6 carbon atoms. Examples of (C₃₋₆)cycloalkyl groups are cyclopropyl, cyclobutyl, cyclopentyl or cyclohexyl. Preferred is cyclopropyl.

The term "heteroaryl", alone or in combination, means a 5- to 10-membered monocyclic or bicyclic aromatic ring containing for example 1, 2 or 3 heteroatoms selected from oxygen, nitrogen and sulfur which may be the same or different. Preferred are monocyclic aromatic rings. Examples of such heteroaryl groups are furanyl, oxazolyl, isoxazolyl, oxadiazolyl, thienyl, thiazolyl, isothiazolyl, thiadiazolyl, pyrrolyl, imidazolyl, pyrazolyl, pyridyl, pyrimidyl, pyridazinyl, pyrazinyl, indolyl, isoindolyl, benzofuranyl, isobenzofuranyl, benzothiophenyl, indazolyl, benzimidazolyl, benzoxazolyl, benzisoxazolyl, benzothiazolyl, benzotriazolyl, benzoxadiazolyl, benzothiadiazolyl, quinolinyl, isoquinolinyl, naphthyridinyl, cinnolinyl, quinazolinyl, quinoxalinyl or phthalazinyl. Preferred heteroaryl groups are: oxazolyl, isoxazolyl, thiazolyl, isothiazolyl, thiadiazolyl, pyrazolyl, pyridyl, pyrimidyl or pyrazinyl. The heteroaryl group may be unsubstituted. The heteroaryl group may also be independently mono- or disubstituted wherein the substituents are independently selected from the group consisting of halogen, (C₁₋₄)alkyl, (C₁₋₄)alkoxy, trifluoromethyl, difluoromethoxy and trifluoromethoxy. Preferred substituents are: halogen, (C₁₋₄)alkyl, (C₁₋₄)alkoxy and trifluoromethyl (more preferred: chlorine, methyl, methoxy and trifluoromethyl).

Preferred is a five or six-membered heteroaryl. Preferred heteroaryl groups are:

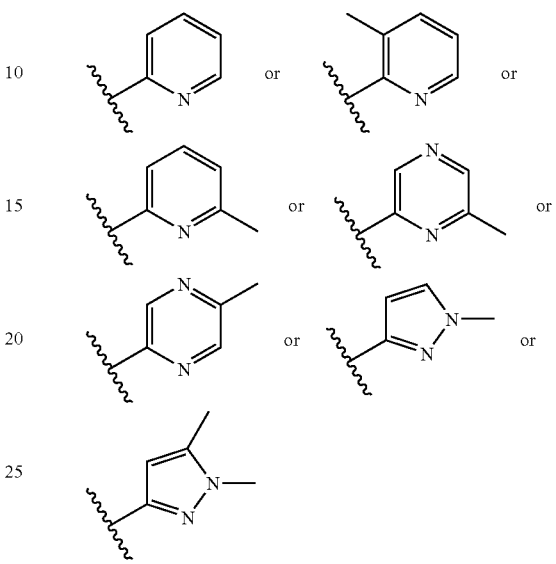

The term "—N(R²)—", alone or in combination, means "—N(H)—" or "—N((C₁₋₄)alkyl)-" wherein the term (C₁₋₄)alkyl has the above meaning. Preferred example is —N(CH₃)—.

The term "—C(H)(R²)—", alone or in combination, means "—C(H)(H)—" or "—C(H)(C₁₋₄)alkyl)-" wherein the term (C₁₋₄)alkyl has the above meaning. Preferred example is —C(H)(CH₃)—.

The term "=C(R²)—", alone or in combination, means "=C(H)—" or "=C(C₁₋₄)alkyl)-" wherein the term (C₁₋₄)alkyl has the above meaning. Preferred example is =C(CH₃)—.

The term "X" preferably represents =C(R²)—, more preferred =C((C₁₋₄)alkyl)-.

The term "Y" preferably represents =N—.

The term "halogen" means fluorine, chlorine, or bromine, preferably fluorine or chlorine, more preferably chlorine.

In case R¹ represents "halogen" the term means fluorine or chlorine, preferably chlorine.

DETAILED DESCRIPTION OF THE INVENTION

Any reference to a compound of formula (I) is to be understood as referring also to enantiomers, mixtures of enantiomers such as racemates, diastereomers, mixtures of diastereomers, diastereomeric racemates, and mixtures of diastereomeric racemates, as well as salts (especially pharmaceutically acceptable salts) and solvates (including hydrates) of such compounds, and morphological forms, as appropriate and expedient.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanesulfonic acid, ethanedisulfonic acid, p-toluenesulfonic acid, salicylic acid, succinic acid, trifluoroacetic acid, and the like that are non toxic to living organisms or, in case the compound of formula (I) is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217. Additionally, compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or polyacid addition salts may be formed.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

A further embodiment of the invention comprises compounds of formula (I), wherein B represents O.

A further embodiment of the invention comprises compounds of formula (I), wherein Z represents —S—.

A further embodiment of the invention comprises compounds of formula (I), wherein $R^2$ represents methyl.

A further embodiment of the invention comprises compounds of formula (I), wherein $R^1$ represents chlorine.

A further embodiment of the invention comprises compounds of formula (I), wherein $R^3$ represents $(C_{1-4})$alkyl, $(C_{3-6})$cycloalkyl or hydroxy$(C_{1-4})$alkyl.

A further embodiment of the invention comprises compounds of formula (I), wherein $R^4$ represents an unsubstituted or mono or di-substituted five or six-membered heteroaryl, substituted with halogen, $(C_{1-4})$alkyl, $(C_{1-4})$alkoxy, trifluoromethyl, difluoromethoxy, or trifluoromethoxy.

A further embodiment of the invention comprises compounds of formula (I), wherein $R^5$ represents $N(CH_3)_2$.

A further embodiment of the invention comprises compounds of formula (I), wherein A represents:

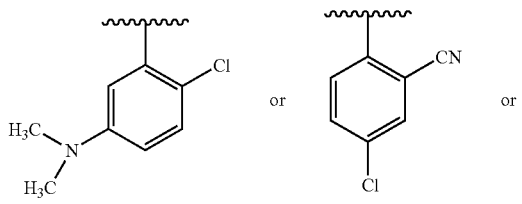

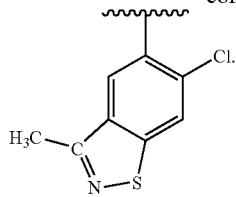

A further embodiment of the invention comprises compounds of formula (I), wherein the compounds are selected from 2-[(2-Chloro-5-dimethylamino-phenyl)-(3,4-dimethoxy-benzenesulfonyl)-amino]-N-ethyl-N-pyridin-2-ylmethyl-acetamide;

2-[(2-Chloro-5-dimethylamino-phenyl)-(3,4-dimethoxy-benzenesulfonyl)-amino]-N-ethyl-N-(6-methyl-pyridin-2-ylmethyl)-acetamide;

2-[(3,4-dimethoxy-benzenesulfonyl)-(5-dimethylamino-2-fluoro-phenyl)-amino]-N-ethyl-N-(6-methyl-pyridin-2-ylmethyl)-acetamide;

2-[(2-Cyano-5-dimethylamino-phenyl)-(3,4-dimethoxy-benzenesulfonyl)-amino]-N-ethyl-N-(6-methyl-pyridin-2-ylmethyl)-acetamide;

2-[(2-Chloro-5-dimethylamino-phenyl)-(3,4-dimethoxy-benzenesulfonyl)-amino]-N-ethyl-N-(6-methyl-pyrazin-2-ylmethyl)-acetamide;

2-[(2-Chloro-5-dimethylamino-phenyl)-(3,4-dimethoxy-benzenesulfonyl)-amino]-N-ethyl-N-(5-methyl-pyrazin-2-ylmethyl)-acetamide;

2-[(2-Chloro-5-dimethylamino-phenyl)-(3,4-dimethoxy-benzenesulfonyl)-amino]-N-ethyl-N-(3-methyl-pyridin-2-ylmethyl)-acetamide;

2-[(2-Chloro-5-dimethylamino-phenyl)-(3,4-dimethoxy-benzenesulfonyl)-amino]-N-ethyl-N-(1-methyl-1H-pyrazol-3-ylmethyl)-acetamide;

2-[(2-Chloro-5-dimethylamino-phenyl)-(3,4-dimethoxy-benzenesulfonyl)-amino]-N-ethyl-N-(1,5-dimethyl-1H-pyrazol-3-ylmethyl)-acetamide;

2-[(4-Chloro-2-cyano-phenyl)-(3,4-dimethoxy-benzenesulfonyl)-amino]-N-ethyl-N-(6-methyl-pyridin-2-ylmethyl)-acetamide;

2-[(6-Chloro-3-methyl-benzo[d]isothiazol-5-yl)-(3,4-dimethoxy-benzenesulfonyl)-amino]-N,N-diethyl-acetamide;

2-[(2-Chloro-5-dimethylamino-phenyl)-(3,4-dimethoxy-benzenesulfonyl)-amino]-N-(2-hydroxy-ethyl)-N-(6-methyl-pyridin-2ylmethyl)-acetamide;

2-[(2-Chloro-5-dimethylamino-phenyl)-(3,4-dimethoxy-benzenesulfonyl)-amino]-N-ethyl-N-(6-methyl-pyrazin-2-ylmethyl)-thioacetamide; and 2-[(2-Chloro-5-isopropenyl-phenyl)-(3,4-dimethoxy-benzenesulfonyl)-amino]-N,N-diethyl-acetamide;

2-[(2-Chloro-5-dimethylamino-phenyl)-(3,4-dimethoxy-benzenesulfonyl)-amino]-N-cyclopropyl-N-(6-methyl-pyridin-2-ylmethyl)-acetamide;

2-[(2-Chloro-5-dimethylamino-phenyl)-(3,4-dimethoxy-benzenesulfonyl)-amino]-N-cyclopropyl-N-(6-methoxy-pyridin-2-ylmethyl)-acetamide;

2-[(2-Chloro-5-dimethylamino-phenyl)-(3,4-dimethoxy-benzenesulfonyl)-amino]-N-cyclopropyl-N-pyridin-2-ylmethyl-acetamide;

2-[(2-Chloro-5-dimethylamino-phenyl)-(3,4-dimethoxy-benzenesulfonyl)-amino]-N-ethyl-N-(5-methyl-thiazol-2-ylmethyl)-acetamide;

2-[(2-Chloro-5-dimethylamino-phenyl)-(3,4-dimethoxy-benzenesulfonyl)-amino]-N-ethyl-N-(2-methyl-oxazol-4-ylmethyl)-acetamide;
2-[(6-Chloro-3-methyl-benzo[d]isothiazol-5-yl)-(3,4-dimethoxy-benzenesulfonyl)-amino]-N-ethyl-N-pyridin-2-ylmethyl-acetamide;
2-[(6-Chloro-3-methyl-benzo[d]isothiazol-5-yl)-(3,4-dimethoxy-benzenesulfonyl)-amino]-N-ethyl-N-(6-methyl-pyridin-2-ylmethyl)-acetamide;
2-[(6-Chloro-3-methyl-benzo[d]isothiazol-5-yl)-(3,4-dimethoxy-benzenesulfonyl)-amino]-N-ethyl-N-(3-methyl-pyridin-2-ylmethyl)-acetamide;
2-[(6-Chloro-3-methyl-benzo[d]isothiazol-5-yl)-(3,4-dimethoxy-benzenesulfonyl)-amino]-N-ethyl-N-(5-methyl-pyrazin-2-ylmethyl)-acetamide;
2-[(6-Chloro-3-methyl-benzo[d]isothiazol-5-yl)-(3,4-dimethoxy-benzenesulfonyl)-amino]-N-ethyl-N-(6-methyl-pyrazin-2-ylmethyl)-acetamide;
2-[(6-Chloro-3-methyl-benzo[d]isothiazol-5-yl)-(3,4-dimethoxy-benzenesulfonyl)-amino]-N-ethyl-N-(1-methyl-1H-pyrazol-3-ylmethyl)-acetamide;
2-[(6-Chloro-3-methyl-benzo[d]isothiazol-5-yl)-(3,4-dimethoxy-benzenesulfonyl)-amino]-N-ethyl-N-(1,5-dimethyl-1H-pyrazol-3-ylmethyl)-acetamide;
2-[(4-Chloro-2-cyano-phenyl)-(3,4-dimethoxy-benzenesulfonyl)-amino]-N,N-diethyl-acetamide;
2-[(4-Chloro-2-cyano-phenyl)-(3,4-dimethoxy-benzenesulfonyl)-amino]-N-cyclopropyl-N-(6-methyl-pyridin-2-ylmethyl)-acetamide;
2-[(2-Chloro-5-dimethylamino-phenyl)-(3,4-dimethoxy-benzenesulfonyl)-amino]-N-ethyl-N-pyrazin-2-ylmethyl-acetamide;
2-[(2-Chloro-5-dimethylamino-phenyl)-(3,4-dimethoxy-benzenesulfonyl)-amino]-N-ethyl-N-pyrimidin-5-ylmethyl-acetamide;
2-[(2-Chloro-5-dimethylamino-phenyl)-(3,4-dimethoxy-benzenesulfonyl)-amino]-N-ethyl-N-thiazol-4-ylmethylamine-acetamide;
2-[(2-Chloro-5-dimethylamino-phenyl)-(3,4-dimethoxy-benzenesulfonyl)-amino]-N-ethyl-N-(5-methyl-[1,3,4]thiadiazol-2-ylmethyl)-acetamide;
2-[(2-Chloro-5-dimethylamino-phenyl)-(3,4-dimethoxy-benzenesulfonyl)-amino]-N-ethyl-N-thiazol-2-ylmethyl-acetamide;
2-[(2-Chloro-5-dimethylamino-phenyl)-(3,4-dimethoxy-benzenesulfonyl)-amino]-N-ethyl-N-(5-methyl-oxazol-2-ylmethyl)-acetamide;
2-[(2-Chloro-5-dimethylamino-phenyl)-(3,4-dimethoxy-benzenesulfonyl)-amino]-N-ethyl-N-isoxazol-5-ylmethyl-acetamide;
2-[(2-Chloro-5-dimethylamino-phenyl)-(3,4-dimethoxy-benzenesulfonyl)-amino]-N-ethyl-N-thiazol-5-ylmethyl-acetamide;
2-[(2-Chloro-5-dimethylamino-phenyl)-(3,4-dimethoxy-benzenesulfonyl)-amino]-N-ethyl-N-(3-fluoro-pyridin-2-ylmethyl)-acetamide;
2-[(2-Chloro-5-dimethylamino-phenyl)-(3,4-dimethoxy-benzenesulfonyl)-amino]-N-ethyl-N-(1-methyl-1H-pyrazol-4-ylmethyl)-acetamide;
2-[(2-Chloro-5-dimethylamino-phenyl)-(3,4-dimethoxy-benzenesulfonyl)-amino]-N-ethyl-N-(1,5-dimethyl-1H-pyrazol-4-ylmethyl)-acetamide;
2-[(2-Chloro-5-dimethylamino-phenyl)-(3,4-dimethoxy-benzenesulfonyl)-amino]-N-(4-chloro-1-methyl-1H-pyrazol-3-ylmethyl)-N-cyclopropyl-acetamide;
2-[(2-Chloro-5-dimethylamino-phenyl)-(3,4-dimethoxy-benzenesulfonyl)-amino]-N-cyclopropyl-(6-methoxy-3-methyl-pyridin-2-ylmethyl)-acetamide;
2-[(2-Chloro-5-dimethylamino-phenyl)-(3,4-dimethoxy-benzenesulfonyl)-amino]-N-ethyl-(2-methyl-thiazol-5-ylmethyl)-acetamide;
2-[(2-Chloro-5-dimethylamino-phenyl)-(3,4-dimethoxy-benzenesulfonyl)-amino]-N-ethyl-(2-methyl-pyrimidin-4-ylmethyl)-acetamide;
2-[(2-Chloro-5-dimethylamino-phenyl)-(3,4-dimethoxy-benzenesulfonyl)-amino]-N-ethyl-(5-methyl-pyridin-3-ylmethyl)-acetamide;
2-[(2-Chloro-5-dimethylamino-phenyl)-(3,4-dimethoxy-benzenesulfonyl)-amino]-N-ethyl-(4-methyl-pyridin-2-ylmethyl)-acetamide;
2-[(2-Chloro-5-dimethylamino-phenyl)-(3,4-dimethoxy-benzenesulfonyl)-amino]-N-ethyl-N-pyridin-3-ylmethyl-acetamide;
2-[(2-Chloro-5-dimethylamino-phenyl)-(3,4-dimethoxy-benzenesulfonyl)-amino]-N-ethyl-N-(1,4-dimethyl-1H-pyrazol-3-ylmethyl)-acetamide;
2-[(2-Chloro-5-dimethylamino-phenyl)-(3,4-dimethoxy-benzenesulfonyl)-amino]-N-ethyl-N-(3-methyl-isoxazol-5-ylmethyl)-acetamide;
2-[(2-Chloro-5-dimethylamino-phenyl)-(3,4-dimethoxy-benzenesulfonyl)-amino]-N-ethyl-N-isoxazol-3-ylmethyl-acetamide;
2-[(2-Chloro-5-dimethylamino-phenyl)-(3,4-dimethoxy-benzenesulfonyl)-amino]-N-ethyl-N-(3-methyl-isothiazol-5-ylmethyl)-acetamide;
2-[(2-Chloro-5-dimethylamino-phenyl)-(3,4-dimethoxy-benzenesulfonyl)-amino]-N-ethyl-N-isothiazol-5-ylmethyl-acetamide;
2-[(2-Chloro-5-dimethylamino-phenyl)-(3,4-dimethoxy-benzenesulfonyl)-amino]-N-ethyl-N-isothiazol-3-ylmethyl-acetamide;
2-[(2-Chloro-5-dimethylamino-phenyl)-(3,4-dimethoxy-benzenesulfonyl)-amino]-N-ethyl-N-(4-methyl-isoxazol-5-ylmethyl)-acetamide;
2-[(2-Chloro-5-dimethylamino-phenyl)-(3,4-dimethoxy-benzenesulfonyl)-amino]-N-ethyl-N-(6-trifluoromethyl-pyridin-2-ylmethyl)-acetamide;
2-[(2-Chloro-5-dimethylamino-phenyl)-(3,4-dimethoxy-benzenesulfonyl)-amino]-N-(2-hydroxy-ethyl)-N-pyridin-2-ylmethyl-acetamide;
2-[(2-Chloro-5-dimethylamino-phenyl)-(3,4-dimethoxy-benzenesulfonyl)-amino]-N-ethyl-N-(5-methyl-isoxazol-3-ylmethyl)-acetamide;
2-[(2-Chloro-5-dimethylamino-phenyl)-(3,4-dimethoxy-benzenesulfonyl)-amino]-N,N-diethyl-acetamide;
2-[(2-Cyano-5-dimethylamino-phenyl)-(3,4-dimethoxy-benzenesulfonyl)-amino]-N,N-diethyl-acetamide;
2-[(2-Chloro-5-dimethylamino-phenyl)-(3,4-dimethoxy-benzenesulfonyl)-amino]-N-ethyl-N-(6-methoxy-pyridin-2-ylmethyl)-acetamide;
2-[(3,4-dimethoxy-benzenesulfonyl)-(5-dimethylamino-2-fluoro-phenyl)-amino]-N-ethyl-N-pyridin-2-ylmethyl-acetamide.

Compounds as described above have $IC_{50}$ values below 50 nM at least on one of the orexin receptor, which have been determined with the FLIPR (Fluorometric Imaging Plates Reader) method described in the experimental section. Preferred compounds are active against both, the $OX_1$ and $OX_2$ receptors. Particularly preferred compounds have $IC_{50}$ values below 20 nM on $OX_1$ and $OX_2$ receptors.

The compounds according to formula (I) are useful in the preparation of a medicament for the prevention or treatment of diseases selected from the group consisting of sleep disorders including insomnias; parasomnias; disturbed biological and circadian rhythms; narcolepsy; sleep disturbances associated with neurological disturbances such as neuropathic pain and restless leg syndrome; obstructive and non obstructive sleep apnea; idiopathic insomnias; insomnias related to psychiatric disorders including dysthymic, mood, psychotic and anxiety disorders; addictions; generalized anxiety, all types of phobias, obsessive compulsive disorder, panic anxiety, post-traumatic stress disorders; affective neurosis; depressive neurosis; anxiety neurosis; schizophrenia and psychosis; attention deficit and hyperactivity disorder; manic depression; delirium; all types of addictions to psychoactive substances or natural reward; sexual dysfunction; psychosexual dysfunction; pathological gambling; tolerance and dependence to narcotics or withdrawal from narcotics; dissociative disorders; adjustment and personality disorders; of metabolic disorders non exhaustively including diabetes and appetite, taste, eating, or drinking disorders; hypothalamic diseases; hyperthermic syndromes; food and/or fluid addiction; polydipsia; dysmetabolic disorders; vomiting/nausea; inflammatory bowel disease; obesities; somatoform disorders; gastric dyskinesia; gastric ulcers; Froehlich's syndrome; hypophysis diseases, hypothalamic hypogonadism; Kallman's syndrome (anosmia, hyposmia); of neurodegenerative and cerebrovascular disorders non comprehensively including all dementias and cognitive dysfunctions in the healthy population and in psychiatric and neurologic disorders; severe mental retardation and dyskinesias such as Huntington's disease and Tourette syndrome; traumatic lesions; demyelinating diseases; brain tumors; Parkinson's disease and neurodegenerative disorders including nosological entities such as disinhibition-dementia-parkinsonism-amyotrophy complex; epilepsies; pallido-ponto-nigral degeneration epilepsy, seizure disorders migraine; headache; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection, HIV; spinal/cranial nerves diseases; muscular diseases; post-chemotherapy pain; post-stroke pain; post-operative pain; neuralgia; conditions associated with visceral pain such as irritable bowel syndrome, migraine and angina; cardiovascular disorders; heart and lung diseases, acute and congestive heart failure; hypotension; hypertension; osteoporosis; angina pectoris; myocardial infarction; ischemic or haemorrhagic stroke; subarachnoid hemorrhage; chronic renal failure; renal disease; impaired glucose tolerance; Cushing's syndrome/disease; basophil adenoma; prolactinoma; hyperprolactinemia; hypopituitarism; hypophysis tumour/adenoma; hypothalamic diseases; functional or psychogenic amenorrhea; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; urinary retention; urinary bladder incontinence e.g. urge incontinence; benign prostatic hypertrophy; ulcers; allergies; asthma; and other medical conditions related to general orexin system dysfunctions occurring in the infant, children, adolescent, adult or elderly population.

Compounds of formula (I) are particularly suitable for use in the treatment of diseases or disorders selected from the group consisting of eating and/or drinking disorders, all types of sleep disorders, all kinds of cognitive dysfunctions in the healthy population and in psychiatric and neurologic disorders.

Eating disorders comprise metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake, including alcohol.

Sleep disorders include all types of insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress, grief, pain or illness.

Cognitive dysfunctions include deficits in all types of attention, learning and memory functions, at all stages of memory formation and consolidation occurring transiently or chronically in the normal, healthy, young, adult or aging population, and also occurring transiently or chronically in psychiatric, neurologic, cardiovascular and immune disorders. Indications include learning disabilities and memory impairment due to toxicant exposure, brain injury, age, neurodegeneration, autoimmunity, schizophrenia, anxiety, depression, epilepsy, mental retardation in children, Down's Syndrome and senile dementia, including Alzheimer's disease, anterior Communicating Artery Syndrome and other stroke syndromes. Indications may also include prophylaxis against memory impairment consecutive to ischemia or hypoxia, reduced blood flow or blood volume (including heart bypass surgery or diseases involving reduced or impaired cardiac output) or exposure to low oxygen conditions. Any therapeutic indication with clinical manifestations of cognitive dysfunction, expressed as deficits in any form or stage of attention, learning or memory linked to medical conditions in young, adult and elderly people.

A further aspect of the invention is a pharmaceutical composition containing at least one compound according to formula (I) and a pharmaceutically acceptable carrier material. Another aspect of the present invention is a method for the treatment or prophylaxis of diseases, which are related to the orexin receptors such as eating disorders or sleep disorders comprising the administration to a patient a therapeutically effective amount of a compound of formula (I).

The compounds of general formula (I) and their pharmaceutically acceptable salts can be used as medicaments, e.g. in the form of pharmaceutical compositions for enteral or parental administration.

The compounds of general formula (I) are useful for the treatment and/or prevention of the diseases mentioned herein.

In one embodiment, the invention relates to a method for the treatment and/or prevention of the diseases mentioned herein, said method comprising administering to a subject a pharmaceutically active amount of a compound of general formula (I).

The compounds according to general formula (I) are useful in the preparation of a medicament for the prevention or treatment of diseases selected from the group consisting of dysthymic disorders including major depression and cyclothymia, affective neurosis, all types of manic depressive disorders, delirium, psychotic disorders, schizophrenia, catatonic schizophrenia, delusional paranoia, adjustment disorders and all clusters of personality disorders; schizoaffective disorders; anxiety disorders including generalized anxiety, obsessive compulsive disorder, posttraumatic stress disorder, panic attacks, all types of phobic anxiety and avoidance; separation anxiety; all psychoactive substance use, abuse, seeking and reinstatement; all types of psychological or physical addictions, dissociative disorders including multiple personality syndromes and psychogenic amnesias; sexual and reproductive dysfunction; psychosexual dysfunction and addiction; tolerance to narcotics or withdrawal from narcotics; increased anaesthetic risk, anaesthetic responsiveness; hypothalamic-adrenal dysfunctions; disturbed biological and circadian rhythms; sleep disturbances associated with diseases such as neurological disorders including neuropathic pain and restless leg syndrome; sleep apnea; narcolepsy; chronic fatigue syndrome; insomnias related to psychiatric disorders; all types of idiopathic insomnias and parasomnias; sleep-wake schedule disorders including jet-lag; all dementias and cognitive dysfunctions in the healthy population and in psychiatric and neurological disorders; mental dysfunctions of aging; all types of amnesia; severe mental retardation; dyskinesias and muscular diseases; muscle spasticity, tremors, movement disorders; spontaneous and medication-induced dyskinesias; neurodegenerative disorders including Huntington's, Creutzfeld-Jacob's, Alzheimer's diseases and Tourette syndrome; Amyotrophic lateral sclerosis; Parkinson's disease; Cushing's syndrome; traumatic lesions; spinal cord trauma; head trauma; perinatal hypoxia; hearing loss; tinnitus; demyelinating diseases; spinal and cranial nerve diseases; ocular damage; retinopathy; epilepsy; seizure disorders; absence seizures, complex partial and generalized seizures; Lennox-Gastaut syndrome; migraine and headache; pain disorders; anaesthesia and analgesia; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; dental pain; pain related to infection e.g. by HIV; post-chemotherapy pain; post-stroke pain; post-operative pain; neuralgia; osteoarthritis; conditions associated with visceral pain such as irritable bowel syndrome; eating disorders; diabetes; toxic and dysmetabolic disorders including cerebral anoxia, diabetic neuropathies and alcoholism; appetite, taste, eating, or drinking disorders; somatoform disorders including hypochondriasis; vomiting/nausea; emesis; gastric dyskinesia; gastric ulcers; Kallman's syndrome (anosmia); impaired glucose tolerance; intestinal motility dyskinesias; hypothalamic diseases; hypophysis diseases; hyperthermia syndromes, pyrexia, febrile seizures, idiopathic growth deficiency; dwarfism; gigantism; acromegaly; basophil adenoma; prolactinoma; hyperprolactinemia; brain tumors, adenomas; benign prostatic hypertrophy, prostate cancer; endometrial, breast, colon cancer; all types of testicular dysfunctions, fertility control; reproductive hormone abnormalities; hot flashes; hypothalamic hypogonadism, functional or psychogenic amenorrhea; urinary bladder incontinence asthma; allergies; all types of dermatitis, acne and cysts, sebaceous gland dysfunctions; cardiovascular disorders; heart and lung diseases, acute and congestive heart failure; hypotension; hypertension; dyslipidemias, hyperlipidemias, insulin resistance; urinary retention; osteoporosis; angina pectoris; myocardial infarction; arrhythmias, coronary diseases, left ventricular hypertrophy; ischemic or haemorrhagic stroke; all types of cerebrovascular disorders including subarachnoid hemorrhage, ischemic and hemorrhagic stroke and vascular dementia; chronic renal failure and other renal diseases; gout; kidney cancer; urinary incontinence; and other diseases related to general orexin system dysfunctions.

Compounds of general formula (I) are particularly suitable for use in the treatment of diseases or disorders selected from the group consisting of all types of sleep disorders, of stress-related syndromes, of psychoactive substance use and abuse, of cognitive dysfunctions in the healthy population and in psychiatric and neurologic disorders, of eating or drinking disorders. Eating disorders may be defined as comprising metabolic dysfunction; dysregulated appetite control; compulsive obesities; emeto-bulimia or anorexia nervosa. Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake. Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance; psychoactive substance use, abuse, seeking and reinstatement are defined as all types of psychological or physical addictions and their related tolerance and dependence components. Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders.

In a further preferred embodiment of the invention compounds of general formula (I) are particularly suitable for use in the treatment of diseases or disorders selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders.

In another preferred embodiment of the invention compounds of general formula (I) are particularly suitable for use in the treatment of diseases or disorders selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In another preferred embodiment of the invention compounds of general formula (I) are particularly suitable for use in the treatment of diseases or disorders selected from the group consisting of eating disorders that comprise metabolic dysfunction; dysregulated appetite control; compulsive obesities; emeto-bulimia or anorexia nervosa.

In another preferred embodiment of the invention compounds of general formula (I) are particularly suitable for use in the treatment of diseases or disorders selected from the group consisting of psychoactive substance use and abuse that comprise all types of psychological or physical addictions and their related tolerance and dependence components.

The present invention also concerns a process for the preparation of a pharmaceutical composition comprising a compound of general formula (I) by mixing one or more active ingredients according to formula (I) with a carrier material in a manner known per se.

The compounds of formula (I) and their pharmaceutically acceptable salts can be used as medicament (e.g. in the form of pharmaceutical preparations). The pharmaceutical preparations can be administered enterally, such as orally (e.g. in the form of tablets, coated tablets, dragées, hard and soft gelatine capsules, solutions, emulsions or suspensions), nasally (e.g. in the form of nasal sprays) or rectally (e.g. in the form of suppositories). However, the administration can also be effected parenterally, such as intramuscularly or intravenously (e.g. in the form of injection solutions), or topically (e.g. in the form of ointments, creams or oils). The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of Formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

A further aspect of the invention is a process for the preparation of compounds of formula (I). Compounds according to formula (I) of the present invention can be prepared according to the general sequence of reactions outlined in the schemes below wherein A, B, X, Y, Z, $R^1$, $R^2$, $R^3$, $R^4$, and $R^5$ are as defined in the description of formula (I), and wherein V is as defined in the description of formula (I). The compounds obtained may also be converted into pharmaceutically acceptable salts thereof in a manner known per se.

The compounds of formula (I) with B is O, may be prepared starting from the respective aniline by reaction with 3,4-dimethoxybenzenesulfonyl chloride. The aniline derivatives may be prepared by reduction of the corresponding nitro compound (Béchamp reduction) (Hamilton C. S. et al *Org. React.* 1944, 2, 428).

The resulting sulfonamide intermediates are transformed to compounds of formula (I) by either alkylation with tert-butyl bromoacetate ester, cleavage under acidic conditions followed by amidation formation with the respective $R^3$—NH—$CH_2$—$R^4$ in the presence of a coupling agent such as PyBOP (scheme 1).

Scheme 1

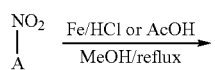

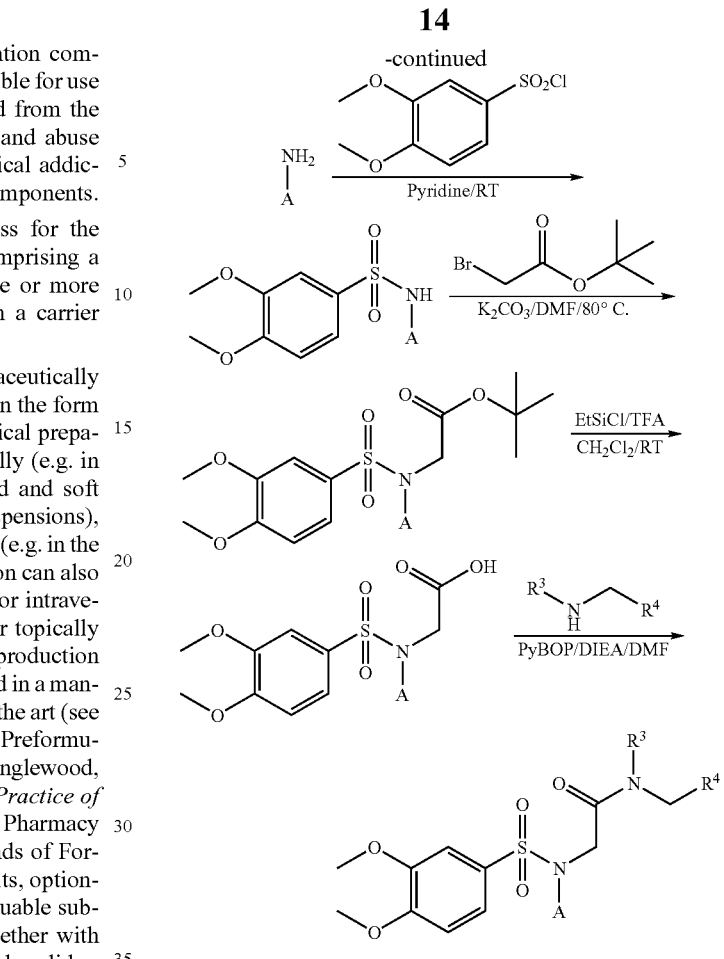

Starting compound A-$NO_2$ may be synthesized according to the experimental section, according to the cited references, or is commercially available.

The secondary amines of formula $R^3$—NH—$CH_2$—$R^4$ may be prepared either by reductive amination with the corresponding aldehyde (method A in scheme 2) or by alkylation with the corresponding halide (method B in scheme 2).

Scheme 2

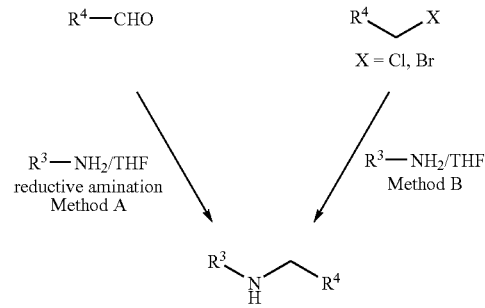

The compounds of the formula $R^4$—CHO, $R^4CH_2X$ and/or $R^3$—$NH_2$ may be synthesized according to the experimental section, according to the cited references, or is commercially available.

The compounds of formula (I) wherein $R^3$ represents ethyl and $R^4$ represents methyl may be prepared by reaction of the sulfonamide intermediate with 2-chloro-N,N-diethyl acetamide under basic reaction conditions (scheme 3).

Scheme 3

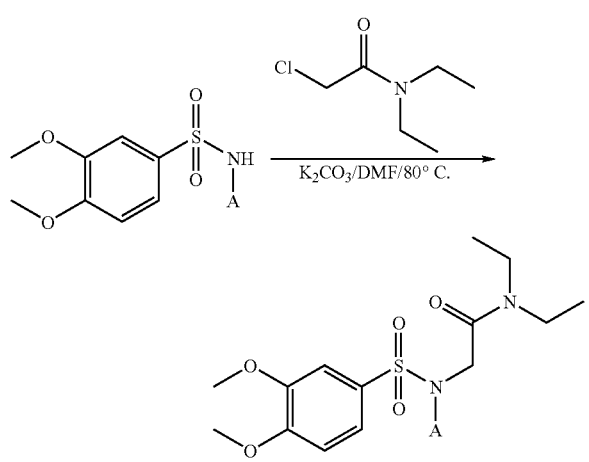

The compounds of formula (I) wherein B represents S may be prepared by reaction of the corresponding acetamide with phosphorus pentasulfide (scheme 4).

Scheme 4

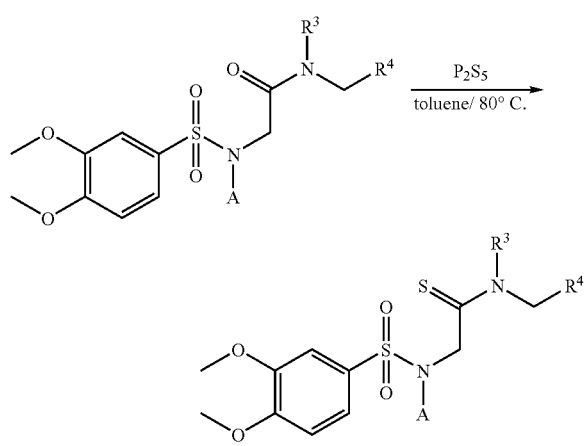

EXPERIMENTAL SECTION

| Abbrevations: | |
|---|---|
| br | broad (NMR) |
| BSA | Bovine serum albumine |
| CHO | Chinese hamster ovary |
| conc | Concentrated |
| d | day(s) |
| d | doublet (NMR) |
| DCM | Dichloromethane |
| DIEA | Disopropylethylamine |
| DMA | N,N-dimethylacetamide |
| DMAP | 4-Dimethylaminopyridine |
| DMF | N,N-dimethylformamide |
| DMSO | Dimethyl sulfoxide |
| EA | Ethyl acetate |
| eq | Equivalent(s) |
| ES | Electron spray |
| Ether | Diethylether |
| EtOH | Ethanol |

| Abbrevations: | |
|---|---|
| FC | Flash chromatography |
| FCS | Foatal calf serum |
| FLIPR | Fluorescent imaging plate reader |
| h | Hour(s) |
| HBSS | Hank's balanced salt solution |
| HEPES | 4-(2-hydroxyethyl)-piperazine-1-ethanesulfonic acid |
| HPLC | High performance liquid chromatography |
| LC | Liquid chromatography |
| m | multiplet (NMR) |
| M | Molar(ity) |
| MeOH | Methanol |
| min | Minute(s) |
| MS | Mass spectroscopy |
| PyBOP | (Benzotriazole-lyloxy)-tripyrrolidinophosphonium-hexafluorophosphate |
| q | quartet (NMR) |
| rt | Retention time |
| RT | Room temperature |
| s | singlet (NMR) |
| sat | Saturated |
| $SiO_2$ | Silica gel |
| t | triplet (NMR) |
| TFA | Trifluoroacetic acid |

I-Chemistry.

The following examples illustrate the preparation of pharmacologically active compounds of the invention but do not at all limit the scope thereof.

All temperatures are stated in ° C.

All the analytical HPLC investigations on non-chiral phases are performed using RP-$C_{18}$ based columns. Analytical HPLC investigations are performed on an instrument with cycle-times of ~2.5 min. NMR measurements are done with a Varian Mercury 300 Instrument.

A Synthesis of [(2-chloro-5-dimethylamino-phenyl)-(3,4-dimethoxy-benzenesulfonyl)-amino]-acetic acid 1) Synthesis of 4-(chloro-3-nitro phenyl)-dimethyl-amine To a cooled (~0° C.) solution of 4-chloro-3-nitroaniline (3 g) in dry DMF (60 mL), was added portionwise NaH 60% (in mineral oil) (1.53 g) and slowly iodomethane (3.25 mL). The resulting reaction mixture was allowed to warm to RT overnight under nitrogen.

The reaction mixture was partitioned between water/ether, the aqueous phase was extracted with ether. The combined organic extracts were washed with brine, dried (MgSO$_4$), filtered and concentrated to yield a crude yellow-brown oil.

FC (EA/n-heptane: 1/9 to 2/8) gave 2034 mg, 58% of the title compound as orange crystals.

$^1$H-NMR (CDCl$_3$): δ=3.00 (s, 6H); 6.75 (dd, 1H), 7.1 (d, 1H); 7.3 (d, 1H).

2) Synthesis of 4-chloro-N',N'-dimethyl-benzene-1,3-diamine

To a solution of 4-(chloro-3-nitro-phenyl)-dimethyl-amine (2.023 g) conc. HCl (7.2 mL) in dry MeOH (11.7 mL), was added portionwise iron powder (~325 mesh) (1.69 g). After the addition, the mixture was stirred at reflux for 10 h.

After cooling to RT, the reaction mixture was poured into ice-water, basified with NaOH 1M until pH 5-7, and filtered over celite. The filtrate was extracted several times with EA. The combined organic extracts were washed with brine, dried (MgSO$_4$), filtered and concentrated to yield the title compound as an oil (1.72 g, 100%).
$^1$H-NMR (CDCl$_3$): δ=2.95 (s, 6H); 6.2 (d, 1H); 6.35 (s, 1H); 7.15 (d, 1H).

3) Synthesis of N-(2-chloro-5-dimethylamino-phenyl)-3,4-dimethoxy-benzenesulfonamide To a solution 4-chloro-N',N'-dimethyl-benzene-1,3-diamine of (1.71 g) in pyridine (5 mL) was added a solution of 3,4-dimethoxybenzenesulfonyl chloride (2.61 g) in pyridine (5 mL). The resulting reaction mixture was stirred at RT under nitrogen for 2 d. The reaction mixture was then diluted with EA, washed with HCl 1M until pH~2-3, the organic phase was washed with water, brine, dried (MgSO$_4$), filtered and concentrated to yield the title compound as a brown foam (3.45 g, 82%) which was used for the next step without further purification. LC-MS: rt=0.90 min. 371 (M+1, ES+).

4) Synthesis of [(2-chloro-5-dimethylamino-phenyl)-(3,4-dimethoxy-benzenesulfonyl)-amino]-acetic acid tert-butylester A mixture of N-(2-chloro-5-dimethylamino-phenyl)-3,4-dimethoxy-benzenesulfonamide (914 mg), tert-butyl bromoacetate (0.4 mL), anhydrous K$_2$CO$_3$ (0-343 g) in dry DMF (6 mL) was stirred at 80° C. for 2 h30.
After cooling to RT, the reaction mixture was diluted with EA, washed with water, brine, dried (MgSO$_4$), filtered and concentrated to yield a crude orange oil.
FC (EA/n-heptane: 1/1) gave 1.17 g, (97%) of the title compound as a beige solid.
LC-MS: rt=1.05 min, 485 (M+1. ES+).

5) Synthesis of [(2-chloro-5-dimethylamino-phenyl)-(3,4-dimethoxy-benzenesulfonyl)-amino]-acetic acid To a solution of [(2-chloro-5-dimethylamino-phenyl)-(3,4-dimethoxy-benzenesulfonyl)-amino]-acetic acid tert-butylester (1.160 g) in dry DCM (5.5 mL) were added successively triethylsilane (0.423 mL) and TFA (4.8 mL).
The reaction mixture was stirred at RT for 4 h and then concentrated under reduced pressure.
The resulting residue was washed with DCM/water, the organic extract was dried (MgSO$_4$), filtered and concentrated to yield 0.98 g (95%) of the title compound as a light brown powder.
LC-MS: rt=0.87 min, 428 (M, ES+).

B Synthesis of [(2-fluoro-5-dimethylamino-phenyl)-(3,4-dimethoxy-benzenesulfonyl)-amino]-acetic acid

1) Synthesis of 4-(fluoro-3-nitro-phenyl)-dimethyl-amine

The title compound was prepared according to the general procedure used for the preparation of 4-(chloro-3-nitro-phenyl)-dimethyl-amine using 4-fluoro-2-nitroaniline in place of 4-chloro-2-nitroaniline.
$^1$H-NMR (CDCl$_3$): δ=3.00 (s, 6H); 7.85 (m, 1H); 7.15 (t, 1H); 7.25 (m, 1H).

2) Synthesis of 4-fluoro-N',N'-dimethyl-benzene-1,3-diamine

The title compound was prepared according to the general procedure used for the preparation of 4-chloro-N',N'-dimethyl-benzene-1,3-diamine.
$^1$H-NMR (CDCl$_3$): δ=2.85 (s, 6H); 3.65 (br.s, 2H); 6.1 (m, 1H); 6.2 (m, 1H); (t, 1H).

3) Synthesis of N-(2-fluoro-5-dimethylamino-phenyl)-3,4-dimethoxy-benzenesulfonamide The title compound was prepared according to the general procedure used for the preparation of N-(2-chloro-5-dimethylamino-phenyl)-3,4-dimethoxy-benzenesulfonamide.
LC-MS: rt=0.71 min, 355 (M+1, ES+).

4) Synthesis of [(2-fluoro-5-dimethylamino-phenyl)-(3,4-dimethoxy-benzenesulfonyl)-amino]-acetic acid tert-butylester The title compound was prepared according to the general procedure used for the preparation of [(2-chloro-5-dimethylamino-phenyl)-(3,4-dimethoxy-benzenesulfonyl)-amino]-acetic acid tert-butylester.
LC-MS: rt=0.99 min, 469 (M+1, ES+).

5) Synthesis of [(2-fluoro-5-dimethylamino-phenyl)-(3,4-dimethoxy-benzenesulfonyl)-amino]-acetic acid The title compound was prepared according to the general procedure used for the preparation of [(2-chloro-5-dimethylamino-phenyl)-(3,4-dimethoxy-benzenesulfonyl)-amino]-acetic acid.
LC-MS: rt=0.77 min, 413 (M+1, ES+).

C Synthesis of [(2-cyano-5-dimethylamino-phenyl)-(3,4-dimethoxy-benzenesulfonyl)-amino]-acetic acid

1) Synthesis of 4-dimethylamino-2-nitro-benzonitrile

To a solution of 4-(chloro-3-nitro-phenyl)-dimethyl-amine (5 g) in dry DMA (25 mL) was added CuCN (2.59 g). The reaction mixture was stirred at reflux for 6 h. After cooling to RT, the reaction mixture was poured into ice-water, the resulting precipitate was filtered off and stirred at reflux for 3 h in a mixture DCM/MeOH (1/1). After cooling, the solution was filtered over celite and concentrated under reduced pressure. The residue was dissolved in DCM, washed with water, the organic phase was dried (MgSO$_4$), filtered and concentrated to yield a crude oil.
FC (EA/n-heptane: 1/4 to EA) gave 1.58 g (33%) of the title compound as an orange solid.
$^1$H-NMR (DMSO-d$_6$): δ=3.11 (s, 6H); 7.08 (dd, 1H); 7.45 (d, 1H); 7.80 (d, 1H).

2) Synthesis of 2-amino-4-dimethylamino-benzonitrile

The title compound was prepared according to the general procedure used for the preparation of 4-chloro-N',N'-dimethyl-benzene-1,3-diamine.
$^1$H-NMR (DMSO-d$_6$): δ=2.91 (s, 6H); 5.59 (br.s., 2H); 5.97 (d, 1H); 6.04 (dd, 1H); 7.12 (d, 1H).

3) Synthesis of N-(2-cyano-5-dimethylamino-phenyl)-3,4-dimethoxy-benzenesulfonamide The title compound was prepared according to the general procedure used for the preparation of N-(2-chloro-5-dimethylamino-phenyl)-3,4-dimethoxy-benzenesulfonamide.
LC-MS: rt=0.81 min, 363 (M+1, ES+).

4) Synthesis of [(2-cyano-5-dimethylamino-phenyl)-(3,4-dimethoxy-benzenesulfonyl)-amino]-acetic acid tert-butylester The title compound was prepared according to the general procedure used for the preparation of [(2-chloro-5-dimethylamino-phenyl)-(3,4-dimethoxy-benzenesulfonyl)-amino]-acetic acid tert-butylester.

LC-MS: rt=1.02 min, 476 (M+1, ES+).

5) Synthesis of [(2-cyano-5-dimethylamino-phenyl)-(3,4-dimethoxy-benzenesulfonyl)-amino]-acetic acid The title compound was prepared according to the general procedure used for the preparation of [(2-chloro-5-dimethylamino-phenyl)-(3,4-dimethoxy-benzenesulfonyl)-amino]-acetic acid.

LC-MS: rt=0.82 min, 420 (M+1, ES+).

D Synthesis of N-(6-chloro-3-methyl-benzo[d]isothiazol-5-yl)-3,4-dimethoxy-benzenesulfonamide

1) Synthesis of 6-chloro-3-methyl-benzo[d]isothiazol-5-ylamine

To a mixture of 6-chloro-3-methyl-5-nitro-benzo[d]isothiazole (127 mg) (prepared according to U.S. Pat. No. 6,355,796) in MeOH (1.1 mL) and conc HCl (0.43 mL) was added iron powder (93 mg) in portions. After the addition was complete, the reaction mixture was stirred at reflux for 2 h15, and poured into ice-water.

The mixture was basified at 0° C. with 5M NaOH solution and extracted with EA. The organic extract was dried (MgSO$_4$) filtered and concentrated to yield a crude product.

FC (n-heptane/EA 9/1 to 6/4) gave 46 mg (41%) of the title compound. as an oil.

$^1$H-NMR (CDCl$_3$): δ=2.6 (s, 3H); 4.2 (br.s, 2H); 7.2 (s, 1H); 7.8 (s, 1H).

2) Synthesis of N-(6-chloro-3-methyl-benzo[d]isothiazol-5-yl)-3,4-dimethoxy-benzenesulfonamide To a solution of 6-chloro-3-methyl-benzo[d]isothiazol-5-ylamine (46 mg) in pyridine (0.26 mL), was added a solution of 3,4-dimethoxybenzenesulfonyl chloride (35 mg) in pyridine (0.26 mL). The resulting reaction mixture was stirred at RT under nitrogen overnight. The reaction mixture was then diluted with EA, washed well with HCl 1M (pH~2-3), the organic phase was washed with water, brine, dried (MgSO$_4$), filtered and concentrated to yield the title compound as white solid.

LC-MS: rt=0.93 min, 399 (M+1, ES+).

E Synthesis of N-[2-chloro-5-(1-hydroxy-1-methyl-ethyl)-phenyl]-3,4-dimethoxy-benzenesulfonamide

1) Synthesis of (4-chloro-3-nitro-phenyl)-methanol

To a solution of 4-chloro-3-nitrobenzaldehyde (5.0 g, 27 mmol) in EtOH (100 mL) at rt was added portion wise NaBH$_4$ (1.02 g, 1 eq). The mixture was stirred at RT for 2 h, concentrated in vacuo and partitioned between ether and water. The organic layer was washed with brine, dried over MgSO$_4$ and concentrated. The title alcohol was recovered as a brownish solid (4.96 g, 98%).

$^1$H-NMR (CDCl$_3$): δ=4.80 (s, 2H); 7.54 (m, 2H); 7.92 (s, 1H).

2) Synthesis of (3-amino-4-chloro-phenyl)-methanol

To a solution of (4-chloro-3-nitro-phenyl)-methanol (4.96 g, 26.4 mmol) in MeOH (60 mL) and conc HCl (22 ml) was added iron powder (4.43 g, 3 eq) in portions. The mixture was then heated at reflux (65° C.) for 6 h, cooled and poured on ice water. The solution was neutralised with dilute NaOH and filtered. The filtrate was extracted with EA several times. The combined organic layers were washed with brine, dried over MgSO$_4$ and concentrated. The product was recovered as a greyish solid (3.8 g, 92%).

3) Synthesis of N-(2-chloro-5-hydroxymethyl-phenyl)-3,4-dimethoxy-benzenesulfonamide A solution of (3-amino-4-chloro-phenyl)-methanol (2.0 g, 12.7 mmol) in pyridine (26 mL) was treated with 3,4-dimethoxybenzenesulfonyl chloride (3.3 g, 1.1 eq). The solution was stirred at RT overnight. The mixture was then partitioned between EA and 3M HCl. The organic layer was washed with brine, dried over MgSO$_4$ and concentrated. The product was recovered as a brownish foam.

$^1$H-NMR (DMSO-d$_6$): δ=3.72 (s, 3H); 3.82 (s, 3H); 4.42 (2, 2H); 7.05-7.20 (m, 2H); 7.22 (d, 1H); 7.25-7.40 (m, 3H); 9.79 (s, 1H).

4) Synthesis of N-(2-chloro-5-formyl-phenyl)-3,4-dimethoxy-benzenesulfonamide A solution of N-(2-chloro-5-hydroxymethyl-phenyl)-3,4-dimethoxy-benzenesulfonamide (2.53 g, 7 mmol) in DCM/THF (1:1, 16 mL) was treated with MnO$_2$ (12.3 g, 20 eq). The mixture was stirred at RT for 6 h, filtered over Celite and concentrated. The residue purified by chromatography on SiO$_2$ (hex/EA 1:1, EA). The product was recovered as a pinkish oil (1.95 g, 77%).

$^1$H-NMR (DMSO-d$_6$): δ=3.73 (s, 3H); 3.81 (s, 3H); 4.42 (d, 2H); 7.09 (d, 1H); 7.25 (d, 1H); 7.32 (m, 1H); 7.6-7.75 (m, 2H); 7.80 (d, 1H); 9.95 (s, 1H); 10.12 (s, 1H).

5) Synthesis of N-[2-chloro-5-(1-hydroxy-ethyl)-phenyl]-3,4-dimethoxy-benzenesulfonamide To a solution of N-(2-chloro-5-formyl-phenyl)-3,4-dimethoxy-benzenesulfonamide (1.77 g, 5 mmol) in THF (20 mL) at −78° C. was added dropwise a solution of methyl lithium in ether (1.6 M, 8.6 mL, 2.75 eq). The mixture was stirred at −78° C. for 30 min and then allowed to warm to RT. The mixture was partitioned between EA and NH$_4$Cl solution, the aqueous phase was once more extracted with EA and the combined organic layers were dried over MgSO$_4$ and concentrated. The residue was dried under hv to give the desired product (1.8 g, 100%) as a yellowish oil.

LC-MS: rt=3.3 min, 370 (M−1, ES−).

6) Synthesis of N-(5-acetyl-2-chloro-phenyl)-3,4-dimethoxy-benzenesulfonamide A solution of N-[2-chloro-5-(1-hydroxy-ethyl)-phenyl]-3,4-dimethoxy-benzenesulfonamide (1.85 g, 5 mmol) in DCM/THF (1:1, 10 mL) was treated with MnO$_2$ (10.8 g, 25 eq). The mixture was stirred at RT for 7 h, filtered over Celite and concentrated. The residue was purified by chromatography on SiO$_2$ (hex/EA 1:1). The product was recovered as a colourless foam (1.58 g, 86%).

7) Synthesis of N-[2-chloro-5-(1-hydroxy-1-methyl-ethyl)-phenyl]-3,4-dimethoxy-benzenesulfonamide To a solution of N-(5-acetyl-2-chloro-phenyl)-3,4-dimethoxy-benzenesulfonamide (1.4 g, 3.8 mmol) in THF (16 mL) at −78° C. was added dropwise a solution of methyl lithium in ether (1.6 M, 6.5 mL, 2.75 eq). The mixture was stirred at −78° C. for 30 min and then allowed to warm to RT. The mixture was partitioned between EA and NH$_4$Cl solution, the aqueous phase was once more extracted with EA and the combined organic layers were dried over MgSO$_4$ and concentrated. The residue was purified by chromatography on SiO$_2$ (hex/EA 2:1, 1:1) to give the desired product (0.97 g, 67%) as a yellowish foam.
$^1$H-NMR (DMSO-d$_6$): δ=3.71 (s, 3H); 3.81 (s, 3H); 5.10 (s, 1H); 7.09 (d, 1H); 7.18 (d, 1H); 7.20-7.35 (m, 4H); 9.66 (s, 1H).

F Synthesis of [(4-chloro-2-cyano-phenyl)-(3,4-dimethoxy-benzenesulfonyl)-amino]-acetic acid

1) Synthesis of N-(4-chloro-2-cyano-phenyl)-3,4-dimethoxy-benzenesulfonamide The title compound was prepared according to the general procedure used for the preparation of N-(2-chloro-5-dimethylamino-phenyl)-3,4-dimethoxy-benzenesulfonamide.
LC-MS: rt=0.78 min, 353 (M+1, ES+).

2) Synthesis of [(4-chloro-2-cyano-phenyl)-(3,4-dimethoxy-benzenesulfonyl)-amino]-acetic acid tert-butylester The title compound was prepared according to the general procedure used for the preparation of [(2-chloro-5-dimethylamino-phenyl)-(3,4-dimethoxy-benzenesulfonyl)-amino]-acetic acid tert-butylester.
LC-MS: rt=1.05 min, 467 (M+1, ES+).

3) Synthesis of [(4-chloro-2-cyano-phenyl)-(3,4-dimethoxy-benzenesulfonyl)-amino]-acetic acid The title compound was prepared according to the general procedure used for the preparation of [(2-chloro-5-dimethylamino-phenyl)-(3,4-dimethoxy-benzenesulfonyl)-amino]-acetic acid.
LC-MS: rt=0.80 min, 411 (M+1, ES+).

G Synthesis of [(6-chloro-3-methyl[d]isothiazol-5-yl)-(3,4-dimethoxy-benzenesulfonyl)-amino]-acetic acid

1) Synthesis of [(6-chloro-3-methyl-benzo[d]isothiazol-5-yl)-(3,4-dimethoxy-benzenesulfonyl)-amino]-acetic acid tert-butyl ester The title compound was prepared according to the general procedure used for the preparation of [(2-chloro-5-dimethylamino-phenyl)-(3,4-dimethoxy-benzenesulfonyl)-amino]-acetic acid tert-butylester.
LC-MS: rt=1.07 min, 554 (M+MeCN, ES+).

2) Synthesis of [(6-chloro-3-methyl-benzo[d]isothiazol-5-yl)-(3,4-dimethoxy-benzenesulfonyl)-amino]-acetic acid The title compound was prepared according to the general procedure used for the preparation of [(2-chloro-5-dimethylamino-phenyl)-(3,4-dimethoxy-benzenesulfonyl)-amino]-acetic acid.
LC-MS: rt=0.91 min, 456 (M, ES+).

H. Synthesis of the secondary amines R$^4$—CH$_2$—NH—R$^3$ wherein R$^3$ and R$^4$ are as defined in the description of formula (I).
Method A: Reductive Amination (General Procedure).
To 2M solution of ethylamine in THF (1.2 eq) was added a solution of aldehyde (1 eq) in dry MeOH (3 mL/mmol). The reaction mixture was stirred at RT under nitrogen for 24 h. Then was added portionwise NaBH$_4$ (0.6 eq), the stirring at RT was continued for 3 h. Then HCl 1N (2 mL) was added carefully and the reaction mixture was concentrated under reduced pressure. The resulting residue was partitioned between HCl 1N and DCM. The aqueous layer was extracted once again with DCM.
The aqueous layer was basified with sat. NaHCO$_3$ solution and extracted with CHCl$_3$ (3×). The combined organic extracts were dried (Na$_2$SO$_4$), filtered and concentrated to yield the product as a crude oil which was used for the next step without further purification or purified by FC.

1) Synthesis of ethyl-pyridin-2-ylmethyl-amine prepared by reaction of pyridine-2-carboxaldehyde with 2M ethylamine in THF.
$^1$H-NMR (CDCl$_3$): δ=1.15 (t, 3H); 1.9 (br.s, 1H); 2.75 (q, 2H); 3.9 (s, 2H); 7.15 (m, 1H); 7.3 (d, 1H); 7.65 (t, 1H); 8.65 (d, 1H).

2) Synthesis of ethyl-(6-methyl-pyridin-2-ylmethyl)-amine prepared by reaction of 6-pyridine-2-carboxaldehyde with 2M ethylamine in THF.
$^1$H-NMR (CDCl$_3$): δ=1.15 (t, 3H); 1.75 (br.s, 1H); 2.55 (s, 3H); 2.75 (q, 2H); 3.9 (s, 2H); 6.95 (d, 1H); 7.1 (d, 1H); 7.55 (t, 1H).

3) Synthesis of ethyl-(3-methyl-pyridin-2-ylmethyl)-amine prepared by reaction of 3-pyridine-2-carboxaldehyde (prepared according to Ma D. et al *Nuclear Medicine and Biology*, 2002, 29, 91-105) with 2M ethylamine in THF.
FC (DCM/MeOH: 9/1 to 8/2) gave the title compound as an oil.
$^1$H-NMR (CDCl$_3$): δ=1.15 (t, 3H); 2.15 (br.s, 1H); 2.3 (s, 3H); 2.75 (q, 2H); 3.85 (s, 2H); 7.15 (d, 1H); 7.45 (d, 1H); 8.4 (s, 1H).

4) Synthesis of ethyl-(1-methyl-1H-pyrazol-3-ylmethyl)-amine prepared by reaction of 1-methyl-1H-pyrazole-3-carbaldehyde (prepared according to WO2004/058702) with 2M ethylamine in THF.

¹H-NMR (CDCl₃): δ=1.15 (t, 3H); 2.7 (q, 2H); 3.75 (s, 2H); 3.85 (s, 3H); 6.15 (s, 1H); 7.2 (s, 1H).

5) Synthesis of cyclopropyl-(6-methyl-pyridin-2-ylmethyl)-amine prepared by reaction of 6-methylpyridine-2-carbaldehyde with cyclopropylamine
¹H-NMR (CDCl₃): δ=0.55 (m, 4H); 1.25 (m, 1H); 2.45 (s, 3H); 4.25 (s, 2H); 7.25 (d, 1H); 7.45 (d, 1H); 7.85 (t, 1H).

6) Synthesis of cyclopropyl-(6-methoxy-pyridin-2-ylmethyl)-amine prepared by reaction of 6-methoxypyridine-2-carbaldehyde with cyclopropylamine
¹H-NMR (CDCl₃): δ=0.55 (m, 4H); 1.25 (m, 1H); 3.85 (s, 3H); 4.25 (s, 2H); 6.55 (d, 1H); 6.65 (d, 1H); 7.85 (t, 1H).

7) Synthesis of ethyl-(5-methyl-[1,3,4]thiadiazol-2-ylmethyl)-amine prepared by reaction of 5-methyl-[1,3,4]thiadiazole-2-carbaldehyde with 2M ethylamine in THF.
¹H-NMR (CDCl₃): δ=1.15 (t, 3H); 2.65 (m, 5H); 3.95 (s, 2H).

8) Synthesis of ethyl-thiazol-2-ylmethyl-amine prepared by reaction of thiazole-2-carbaldehyde with 2M ethylamine in THF.
¹H-NMR (CDCl₃): δ=1.15 (t, 3H); 2.75 (q, 2H); 4.05 (s, 2H); 7.35 (s, 1H); 7.8 (s, 1H).

9) Synthesis of ethyl-(3-fluoro-pyridin-2-ylmethyl)-amine prepared by reaction of the commercially available 3-fluoro-pyridin-2-carbaldehyde with 2M ethylamine in THF.
¹H-NMR (CDCl₃): δ=1.15 (t, 3H); 2.75 (q, 2H); 3.95 (s, 2H); 7.15-7.30 (m, 2H); 8.45 (s, 1H).

10) Synthesis of ethyl-thiazol-5-ylmethyl-amine prepared by reaction of the commercially available thiazole-5-carbaldehyde with 2M ethylamine in THF.
¹H-NMR (CDCl₃): δ=1.15 (t, 3H); 2.75 (q, 2H); 3.95 (s, 2H); 7.7 (s, 1H); 8.7 (s, 1H).

11) Synthesis of ethyl-(1-methyl-1H-pyrazol-4-ylmethyl)-amine prepared by reaction of the commercially available 1-methyl-1H-pyrazole-4-carbaldehyde with 2M ethylamine in THF.
¹H-NMR (CDCl₃): δ=1.15 (t, 3H); 2.65 (q, 2H); 3.65 (s, 3H); 3.95 (s, 2H); 7.35 (d, 1H); 7.4 (d, 1H).

12) Synthesis of ethyl-(1,5-dimethyl-1H-pyrazol-4-ylmethyl)-amine prepared by reaction of the commercially available 1,5-dimethyl-1H-pyrazole-4-carbaldehyde with 2M ethylamine in THF.

¹H-NMR (CDCl₃): δ=1.15 (t, 3H); 2.2 (s, 3H); 2.65 (q, 2H); 3.55 (s, 3H); 3.8 (s, 2H); 7.35 (s, 1H).

13) Synthesis of (4-chloro-1-methyl-1H-pyrazol-3-ylmethyl)-cyclopropyl-amine prepared by reaction of the commercially available (4-chloro-1-methyl-1H-pyrazole)-3-carbaldehyde with 2M ethylamine in THF.
¹H-NMR (CDCl₃): δ=0.55 (m, 4H); 1.25 (m, 1H); 3.6 (s, 3H); 3.85 (s, 2H); 7.35 (s, 1H).

14) Synthesis of cyclopropyl-(6-methoxy-3-methyl-pyridin-2-ylmethyl)-amine prepared by reaction of (6-methoxy-3-methyl-pyridin)-2-carbaldehyde (Comins D. L. et al *J. Org. Chem.* 1990, 55, 1, 69-73) with cyclopropylamine
¹H-NMR (CDCl₃): δ=0.55 (m, 4H); 1.25 (m, 1H); 2.35 (s, 3H); 3.73 (s, 3H); 4.05 (s, 2H); 6.5 (d, 1H); 7.75 (d, 1H).

15) Synthesis of ethyl-(2-methyl-pyrimidin-4-ylmethyl)-amine prepared by reaction of 2-methyl-pyrimidin-4-carbaldehyde with 2M ethylamine in THF.
¹H-NMR (CDCl₃): δ=1.05 (t, 3H); 2.75 (m, 5H); 3.85 (s, 2H); 7.15 (d, 1H); 8.55 (d, 1H).

16) Synthesis of ethyl-(5-methyl-pyridin-3-ylmethyl)-amine prepared by reaction of 5-methyl-pyridin-3-carbaldehyde (Kemnitzer W. et al *J. Med. Chem.* 2004, 47, 25, 6299-6310) with 2M ethylamine in THF.
¹H-NMR (CDCl₃): δ=1.15 (t, 3H); 2.3 (s, 3H), 2.65 (q, 2H); 3.85 (s, 2H); 7.45 (s, 1H); 8.35 (d, 2H).

17) Synthesis of ethyl-(4-methyl-pyridin-2-ylmethyl)-amine prepared by reaction of the commercially available 4-methyl-pyridin-2-carbaldehyde with 2M ethylamine in THF.
¹H-NMR (CDCl₃): δ=1.15 (t, 3H); 2.35 (s, 3H), 2.75 (q, 2H); 3.85 (s, 2H); 6.95 (s, 1H); 7.1 (d, 1H); 8.35 (d, 1H).

18) Synthesis of ethyl-pyridin-3-ylmethyl-amine prepared by reaction of the commercially available pyridin-3-carbaldehyde with 2M ethylamine in THF.
¹H-NMR (CDCl₃): δ=1.15 (t, 3H); 2.75 (q, 21-1); 3.85 (s, 2H); 7.45 (t, 1H); 7.9 (d, 1H); 8.6 (d, 1H); 8.75 (s, 1H).

19) Synthesis of ethyl-(2-methyl-thiazol-5-ylmethyl)-amine prepared by reaction of 2-methyl-thiazole-5-carbaldehyde (Khanna I. K. et al *J. Med. Chem.* 2000, 43, 16, 3168-3185) with 2M ethylamine in THF.
¹H-NMR (CDCl₃): δ=1.05 (t, 3H); 2.75 (m, 5H); 3.85 (s, 2H); 7.4 (s, 1H).

20) Synthesis of ethyl-(6-trifluoromethyl-pyridin-2-ylmethyl)-amine prepared by reaction of 6-trifluoromethyl-pyridin-2-carbaldehyde (Ashimori A. *Chem. Pharm. Bull.* 1990, 38, 9, 2446-2458) with 2M ethylamine in THF.

¹H-NMR (CDCl₃): δ=1.25 (t, 3H); 2.85 (q, 2H); 3.95 (s, 2H); 7.45 (d, 1H); 7.65 (d, 1H); 7.95 (d, 1H).

21) Synthesis of ethyl-(3-methyl-isothiazol-5-ylmethyl)-amine prepared by reaction of 3-methyl-isothiazole-5-carbaldehyde (Buttimore D. et al *J. Chem. Soc.* 1963, 2032-2039) with 2M ethylamine in THF.
¹H-NMR (CDCl₃): δ=1.15 (t, 3H); 2.45 (s, 3H); 2.75 (q, 2H); 4.05 (s, 2H); 6.85 (s, 1H).

22) Synthesis of 2-[(6-methyl-pyridin-2-ylmethyl)-amino]-ethanol

A mixture of 6-methyl-pyridine-2-carboxaldehyde (500 mg), titanium (IV) isopropoxide (2.14 g), 2M ethylamine (in THF) in dry THF (12 mL) was stirred for 8 h at RT under nitrogen. Then NaBH₄ (428 mg) and EtOH (4 mL) were added, the stirring at RT was continued for 7 h. The reaction mixture was then poured into aqueous ammonia (2M), the resulting inorganic precipitate was filtered and washed with ether. The organic layer was separated and the remaining aqueous layer was extracted with ether. The combined organic extracts were washed with 1M HCl to separate the neutral materials. The acidic aqueous solution was washed once with ether to separate the non-basic impurities, then treated with 2M NaOH to pH 10-12, and extracted with DCM (3×). The combined organic extracts were washed with brine, dried over MgSO₄, filtered and concentrated in vacuo to give 100 mg (16%) of the title compound which was used for the next step without further purification.
¹H-NMR (CDCl₃): δ=2.55 (s, 3H); 2.8 (m, 3H); 3.65 (t, 2H); 3.85 (s, 2H); 7.05 (m, 2H); 7.55 (t, 1H).

23) Synthesis of 2-[(pyridin-2-ylmethyl)-amino]-ethanol prepared as 2-[(6-methyl-pyridin-2-ylmethyl)-amino]-ethanol but reaction with pyridine-2-carboxaldehyde
¹H-NMR (CDCl₃): δ=2.8 (m, 3H); 3.65 (t, 2H); 3.85 (s, 2H); 7.05 (m, 2H); 7.55 (t, 1H).
Method B: Alkylation (General Procedure)
The halide (1 eq) was dissolved in THF (0.2 mL/2.5 mmol) and ethylamine 2M in THF (13 eq) was added. The reaction mixture was stirred for 2 h at RT, diluted with EA and washed with sat. NaHCO₃ solution. The aqueous phase was then extracted with CHCl₃. The combined organic extracts were dried, filtered and concentrated to yield the product as an oil which was used for the next step without further purification.

1) Synthesis of ethyl-(5-methyl-pyrazin-2-ylmethyl)-amine prepared by reaction of 2-chloromethyl-5-methyl-pyrazine (prepared according to Newkome G. R. et al, *Synthesis*, 1984, 676-679) with 2M ethylamine in THF.
¹H-NMR (CDCl₃): δ=1.15 (t, 3H); 2.55 (s, 3H); 2.75 (q, 2H); 3.9 (s, 2H); 8.35 (s, 1H); 8.45 (s, 1H).

2) Synthesis of ethyl-(6-methyl-pyrazin-2-ylmethyl)-amine prepared by reaction of 2-chloromethyl-6-methyl-pyrazine (prepared according to Eiermann U. et al, *Chem. Ber.*, 1990, 123, 523-533) with 2M ethylamine in THF.
¹H-NMR (CDCl₃): δ=1.15 (t, 3H); 2.55 (s, 3H); 2.75 (q, 2H); 3.9 (s, 2H); 8.3 (s, 1H); 8.4 (s, 1H).

3) Synthesis of ethyl-(1,5-dimethyl-pyrazin-2-ylmethyl)-amine prepared by reaction of 3-bromomethyl-1,5-dimethyl-1H-pyrazole (prepared according to Juanes O. et al, *J. Chem. Soc., Chem. Commun.*, 1985, 24, 1765-1766) with 2M ethylamine in THF.
¹H-NMR (CDCl₃): δ=1.15 (t, 3H); 1.4 (br.s, 1H); 2.25 (s, 3H); 2.7 (q, 2H); 3.75 (s, 5H); 5.95 (s, 1H).

4) Synthesis of ethyl-(2-methyl-oxazol-4-ylmethyl)-amine prepared by reaction of 4-bromomethyl-2-methyl-oxazole (prepared according to Pattenden G. et al, *Org. & Biomolecular Chem.*, 2003, 1, 23, 4173-4208) with 2M ethylamine in THF.
¹H-NMR (CDCl₃): δ=1.15 (t, 3H); 2.35 (s, 3H); 2.7 (q, 2H); 3.7 (s, 2H); 7.4 (s, 1H).

5) Synthesis of ethyl-(5-methyl-thiazol-2-ylmethyl)-amine prepared by reaction of 4-bromomethyl-2-methyl-oxazole (prepared according to Pattenden G. et al, *Org. & Biomolecular Chem.*, 2003, 1, 23, 4173-4208) with 2M ethylamine in THF.
¹H-NMR (CDCl₃): δ=1.15 (t, 3H); 2.35 (s, 3H); 2.7 (q, 2H); 3.7 (s, 2H); 7.4 (s, 1H).

6) Synthesis of ethyl-thiazol-4-ylmethyl-amine prepared by reaction of the commercially available 4-chloromethyl-thiazole with 2M ethylamine in THF.
¹H-NMR (CDCl₃): δ=1.15 (t, 3H); 2.65 (q, 2H); 3.95 (s, 2H); 7.15 (s, 1H); 8.8 (s, 1H).

7) Synthesis of ethyl-pyrazin-2-ylmethyl-amine prepared by reaction of the 2-chloromethyl-pyrazine (Newkome G. R. et al *Synthesis* 1984, 8, 676-679) with 2M ethylamine in THF.
¹H-NMR (CDCl₃): δ=1.15 (t, 3H); 2.65 (q, 2H); 3.95 (s, 2H); 8.35 (d, 1H); 8.5 (d, 1H); 8.6 (s, 1H).

8) Synthesis of ethyl-pyrimidin-5-ylmethyl-amine prepared by reaction of the 5-chloromethyl-pyrimidine (Russell M. G. N et al *J. Med. Chem.* 2005, 48, 5, 1367-1383) with 2M ethylamine in THF.
¹H-NMR (CDCl₃): δ=1.15 (t, 3H); 2.65 (q, 2H); 3.95 (s, 2H); 7.35 (d, 1H); 8.65 (d, 1H); 9.15 (s, 1H).

9) Synthesis of ethyl-(5-methyl-oxazol-2-ylmethyl)-amine prepared by reaction of the commercially available 2-chloromethyl-5-methyl-oxazole with 2M ethylamine in THF.
¹H-NMR (CDCl₃): δ=1.15 (t, 3H); 2.25 (s, 3H); 2.65 (q, 2H); 3.95 (s, 2H); 6.6 (s, 1H).

10) Synthesis of ethyl-isoxazol-5-ylmethyl-amine prepared by reaction of the 5-bromomethyl-isoxazole (Deshong P. et al *J. Org. Chem.* 1988, 53, 7, 1356-1364) with 2M ethylamine in THF.

11) Synthesis of ethyl-(3-methyl-isoxazol-5-ylmethyl)-amine prepared by reaction of 5-chloromethyl-3-methyl-isoxazole (Li W.-T. et al *J. Med. Chem.* 2003, 46, 9, 1706-1715) with 2M ethylamine in THF.

$^1$H-NMR (CDCl$_3$): δ=1.15 (t, 3H); 2.75 (q, 2H); 3.9 (s, 2H); 5.95 (s, 1H).

12) Synthesis of ethyl-(4-methyl-isoxazol-5-ylmethyl)-amine prepared by reaction of 5-chloromethyl-4-methyl-isoxazole with 2M ethylamine in THF.

$^1$H-NMR (CDCl$_3$): δ=1.15 (t, 3H); 2.00 (s, 2H); 2.65 (q, 2H); 3.9 (s, 2H); 8.00 (s, 1H).

13) Synthesis of ethyl-isothiazol-5-ylmethyl-amine prepared by reaction of 5-chloromethyl-isothiazole with 2M ethylamine in THF.

$^1$H-NMR (CDCl$_3$): δ=1.15 (t, 3H); 2.75 (q, 2H); 4.05 (s, 2H); 7.05 (d, 1H); 7.9 (d, 1H).

14) Synthesis of ethyl-isothiazol-3-ylmethyl-amine prepared by reaction of 3-bromomethyl-isothiazole (Buttimore D. et al *J. Chem. Soc.* 1965, 7274-7276) with 2M ethylamine in THF.

$^1$H-NMR (CDCl$_3$): δ=1.15 (t, 3H); 2.75 (q, 2H); 4.05 (s, 2H); 7.15 (d, 1H); 8.55 (d, 11-1).

15) Synthesis of (1,4-dimethyl-1H-pyrazol-3-ylmethyl)-ethyl-amine prepared by reaction of 3-chloromethyl-1,4-dimethyl-1H-pyrazole (Calderwood E. F. et al *Synth. Commun.* 2004, 34, 19, 3455-3464) with 2M ethylamine in THF.

$^1$H-NMR (CDCl$_3$): δ=1.25 (t, 3H); 1.95 (s, 3H); 2.05 (s, 3H); 2.85 (q, 2H); 3.85 (s, 2H): 7.05 (s, 1H).

16) Synthesis of (4-methyl-isoxazol-3-ylmethyl)-ethyl-amine prepared by reaction of the commercially available 3-bromomethyl-4-methyl-isoxazole with 2M ethylamine in THF.

$^1$H-NMR (CDCl$_3$): δ=1.15 (t, 3H); 2.35 (s, 3H); 2.75 (q, 2H); 3.85 (s, 2H); 5.95 (s, 1H).

J Synthesis of compounds of formula (I)

J1 Via Alkylation of the Sulfonamide Intermediate with 2-Chloro-N,N-Diethyl Acetamide (General Procedure).

A mixture of the sulfonamide (1 eq), 2-chloro-N,N-diethylacetamide (1 eq), anhydrous K$_2$CO$_3$ (1 eq) in dry DMF (3 mL/mmol) was stirred at 80° C. under nitrogen for 20 h. After cooling to RT, the reaction mixture was diluted with EA, washed with water. The organic extract was washed with brine, dried (MgSO$_4$), filtered and concentrated to give a crude oil which was purified by FC.

Example 1

2-[(6-Chloro-3-methyl-benzo[d]isothiazol-5-yl)-(3,4-dimethoxy-benzenesulfonyl)-amino]-N,N-diethyl-acetamide prepared by reaction of N-(6-chloro-3-methyl-benzo[d]isothiazol-5-yl)-3,4-dimethoxy-benzenesulfonamide.

FC (EA/n-heptane: 1/1 to 1/0) gave the title compound as a white solid.

LC-MS: rt=0.97 min, 513 (M+1, ES+).

Example 2

2-[(2-Chloro-5-isopropenyl-phenyl)-(3,4-dimethoxy-benzenesulfonyl)-amino]-N,N-diethyl-acetamide a) Synthesis of 2-[[2-chloro-5-(1-hydroxy-1-methyl-ethyl)-phenyl]-(3,4-dimethoxy-benzenesulfonyl)-amino]-N,N-diethyl-acetamide To a solution of N-[2-chloro-5-(1-hydroxy-1-methyl-ethyl)-phenyl]-3,4-dimethoxy-benzenesulfonamide (0.98 g, 2.5 mmol) in DMF (7.5 mL) was added 2-Chloro-N,N-diethyl-acetamide (0.418 g, 1.1 eq) and K$_2$CO$_3$ (0.35 g, 1 eq). The mixture was heated at 80° C. over night, cooled and partitioned between EA and water. The organic layer was washed several times with water and brine, dried over MgSO$_4$ and concentrated. The residue was purified by chromatography on SiO$_2$ (hex/EA 1:1, EA) to give the product as a colourless foam (1.15 g, 92%).

$^1$H-NMR (DMSO-d$_6$): δ=0.91 (t, 3H); 1.07 (t, 3H); 1.28 (s, 6H); 3.16 (q, 2H); 3.32 (q, 2H); 3.77 (s, 3H); 3.85 (s, 3H); 4.45 (s, 2H); 5.10 (s, 1H); 7.09 (d, 1H); 7.20 (d, 1H); 7.25 (m, 1H); 7.35-7.45 (m, 3H).

b) Title Compound

To a solution of 2-[[2-chloro-5-(1-hydroxy-1-methyl-ethyl)-phenyl]-(3,4-dimethoxy-benzenesulfonyl)-amino]-N,N-diethyl-acetamide (0.527 g, 1 mmol) in DCM (10 mL) was added at 0° C. NEt$_3$ (0.88 mL, 6 eq) and DMAP (7 mg). Methane sulfonylchloride (0.123 mL, 1.5 eq) was added and the mixture warmed to RT and stirred for 6 h. The mixture was partitioned between DCM and water. The aqueous phase was once more extracted with DCM and the combined organic layers dried over MgSO$_4$ and concentrated. The residue was purified by chromatography on SiO$_2$ (hex/EA 1:1, EA, EA/MeOH 9:1) to give the title compound as a colourless solid (0.186 g, 37%). Unreacted starting material (0.29 g, 55%) was also recovered.

LC-MS: rt=3.87 min, 481 (M+1, ES+).

J2 Via Amidation of the Acid Intermediate with the Secondary Amines R$^4$—CH$_2$—NH—R$^3$ (General Procedure).

A mixture of acid (1 eq), amine R$^4$—CH$_2$—NH—R$^3$ (1 eq), PyBOP (1 eq), DIEA (2.3 eq) in dry DMF (5 mL/mmol) was stirred at RT under nitrogen for 20 h. The reaction mixture was diluted with EA, washed with water. The organic extract was washed with brine, dried (MgSO$_4$), filtered and concentrated to give a crude oil which was purified by FC.

Example 3

2-[(2-Chloro-5-dimethylamino-phenyl)-(3,4-dimethoxy-benzenesulfonyl)-amino]-N-ethyl-N-pyridin-2-ylmethyl-acetamide prepared by reaction of [(2-chloro-5-dimethylamino-phenyl)-(3,4-dimethoxy-benzenesulfonyl)-amino]-acetic acid with ethyl-pyridin-2-ylmethyl-amine.

FC (EA) gave the title compound as a foam.
LC-MS: rt=0.81 min, 548 (M+1, ES+).

Example 4

2-[(2-Chloro-5-dimethylamino-phenyl)-(3,4-dimethoxy-benzenesulfonyl)-amino]-N-ethyl-N-(6-methyl-pyridin-2-ylmethyl)-acetamide prepared by reaction of [(2-chloro-5-dimethylamino-phenyl)-(3,4-dimethoxy-benzenesulfonyl)-amino]-acetic acid with ethyl-(6-methyl-pyridin-2-ylmethyl)-amine.

FC (EA) gave the title compound as a foam.
LC-MS: rt=0.82 min, 562 (M+1, ES+).

Example 5

2-[(3,4-dimethoxy-benzenesulfonyl)-(5-dimethylamino-2-fluoro-phenyl)-amino]-N-ethyl-N-(6-methyl-pyridin-2-ylmethyl)-acetamide prepared by reaction of [(2-fluoro-5-dimethylamino-phenyl)-(3,4-dimethoxy-benzenesulfonyl)-amino]-acetic acid with ethyl-(6-methyl-pyridin-2-ylmethyl)-amine.

FC (EA) gave the title compound as a foam.
LC-MS: rt=0.74 min, 545 (M+1, ES+).

Example 6

2-[(2-Cyano-5-dimethylamino-phenyl)-(3,4-dimethoxy-benzenesulfonyl)-amino]-N-ethyl-N-(6-methyl-pyridin-2-ylmethyl)-acetamide prepared by reaction of [(2-cyano-5-dimethylamino-phenyl)-(3,4-dimethoxy-benzenesulfonyl)-amino]-acetic acid with ethyl-(6-methyl-pyridin-2-ylmethyl)-amine.

FC (EA) gave the title compound as a foam.
LC-MS: rt=0.78 min, 552 (M+1, ES+).

Example 7

2-[(2-Chloro-5-dimethylamino-phenyl)-(3,4-dimethoxy-benzenesulfonyl)-amino]-N-ethyl-N-(6-methyl-pyrazin-2-ylmethyl)-acetamide prepared by reaction of [(2-chloro-5-dimethylamino-phenyl)-(3,4-dimethoxy-benzenesulfonyl)-amino]-acetic acid with ethyl-(6-methyl-pyrazin-2-ylmethyl)-amine.

FC (EA) gave the title compound as a foam.
LC-MS: rt=0.94 min, 563 (M+1, ES+).

Example 8

2-[(2-Chloro-5-dimethylamino-phenyl)-(3,4-dimethoxy-benzenesulfonyl)-amino]-N-ethyl-N-(5-methyl-pyrazin-2-ylmethyl)-acetamide prepared by reaction of [(2-chloro-5-dimethylamino-phenyl)-(3,4-dimethoxy-benzenesulfonyl)-amino]-acetic acid with ethyl-(5-methyl-pyrazin-2-ylmethyl)-amine.

FC (EA) gave the title compound as a foam.
LC-MS: rt=0.94 min, 563 (M+1, ES+).

Example 9

2-[(2-Chloro-5-dimethylamino-phenyl)-(3,4-dimethoxy-benzenesulfonyl)-amino]-N-ethyl-N-(3-methyl-pyridin-2-ylmethyl)-acetamide prepared by reaction of [(2-chloro-5-dimethylamino-phenyl)-(3,4-dimethoxy-benzenesulfonyl)-amino]-acetic acid with ethyl-(3-methyl-pyridin-2-ylmethyl)-amine.

FC (EA) gave the title compound as a foam.
LC-MS: rt=0.82 min, 562 (M+1, ES+).

Example 10

2-[(2-Chloro-5-dimethylamino-phenyl)-(3,4-dimethoxy-benzenesulfonyl)-amino]-N-ethyl-N-(1-methyl-1H-pyrazol-3-ylmethyl)-acetamide prepared by reaction of [(2-chloro-5-dimethylamino-phenyl)-(3,4-dimethoxy-benzenesulfonyl)-amino]-acetic acid with ethyl-(1-methyl-1H-pyrazol-3-ylmethyl)-amine.

FC (EA) gave the title compound as a foam.
LC-MS: rt=0.91 min, 551 (M+1, ES+).

Example 11

2-[(2-Chloro-5-dimethylamino-phenyl)-(3,4-dimethoxy-benzenesulfonyl)-amino]-N-ethyl-N-(1,5-dimethyl-1H-pyrazol-3-ylmethyl)-acetamide prepared by reaction of [(2-chloro-5-dimethylamino-phenyl)-(3,4-dimethoxy-benzenesulfonyl)-amino]-acetic acid with ethyl-(1,5-dimethyl-1H-pyrazol-3-ylmethyl)-amine.

FC (EA) gave the title compound as a foam.
LC-MS: rt=0.95 min, 565 (M+1, ES+).

Example 12

2-[(4-Chloro-2-cyano-phenyl)-(3,4-dimethoxy-benzenesulfonyl)-amino]-N-ethyl-N-(6-methyl-pyridin-2-ylmethyl)-acetamide prepared by reaction of [(4-chloro-5-cyano-phenyl)-(3,4-dimethoxy-benzenesulfonyl)-amino]-acetic acid with ethyl-(6-methyl-pyridin-2-ylmethyl)-amine.

FC (EA) gave the title compound as a foam.
LC-MS: rt=0.82 min, 543 (M, ES+).

Example 13

2-[(2-Chloro-5-dimethylamino-phenyl)-(3,4-dimethoxy-benzenesulfonyl)-amino]-N-(2-hydroxyethyl)-N-(6-methyl-pyridin-2-ylmethyl)-acetamide prepared by reaction of [(2-chloro-5-dimethylamino-phenyl)-(3,4-dimethoxy-benzenesulfonyl)-amino]-acetic acid with. 2-[(6-methyl-pyridin-2-ylmethyl)-amino]-ethanol.
FC (EA) gave the title compound as a foam.
LC-MS: rt=0.77 min, 577 (M+1, ES+).

Example 14

2-[(2-Chloro-5-dimethylamino-phenyl)-(3,4-dimethoxy-benzenesulfonyl)-amino]-N-ethyl-N-(6-methyl-pyrazin-2-ylmethyl)-thioacetamide To a solution of 2-[(2-chloro-5-dimethylamino-phenyl)-(3,4-dimethoxy-benzenesulfonyl)-amino]-N-ethyl-N-(6-methyl-pyrazin-2-ylmethyl)-acetamide (20 mg) in dry toluene (0.2 mL) was added in one portion phosphorus pentasulfide (10 mg). The reaction mixture was stirred at 80° C. under nitrogen for 3 h. After cooling to RT, the reaction mixture was concentrated under reduced pressure and the residue was purified by FC (EA/n-heptane: 8/2 to EA) to give 12 mg (57%) of the title compound as a foam.
LC-MS: rt=1.03 min, 579 (M+1, ES+).

Example 15

2-[(2-Chloro-5-dimethylamino-phenyl)-(3,4-dimethoxy-benzenesulfonyl)-amino]-N-cyclopropyl-N-(6-methyl-pyridin-2-ylmethyl)-acetamide prepared by reaction of [(2-chloro-5-dimethylamino-phenyl)-(3,4-dimethoxy-benzenesulfonyl)-amino]-acetic acid with.cyclopropyl-(6-methyl-pyridin-2-ylmethyl)-amine
FC (EA) gave the title compound as a foam.
LC-MS: rt=0.95 min, 573 (M, ES+).

Example 16

2-[(2-Chloro-5-dimethylamino-phenyl)-(3,4-dimethoxy-benzenesulfonyl)-amino]-N-cyclopropyl-N-(6-methoxy-pyridin-2-ylmethyl)-acetamide prepared by reaction of [(2-chloro-5-dimethylamino-phenyl)-(3,4-dimethoxy-benzenesulfonyl)-amino]-acetic acid with.cyclopropyl-(6.methoxy-pyridin-2-ylmethyl)-amine
FC (EA) gave the title compound as a foam.
LC-MS: rt=0.95 min, 589 (M, ES+).

Example 17

2-[(2-Chloro-5-dimethylamino-phenyl)-(3,4-dimethoxy-benzenesulfonyl)-amino]-N-cyclopropyl-N-pyridin-2-ylmethyl-acetamide prepared by reaction of [(2-chloro-5-dimethylamino-phenyl)-(3,4-dimethoxy-benzenesulfonyl)-amino]-acetic acid with.commercially available cyclopropyl-pyridin-2-ylmethyl-amine.
FC (EA) gave the title compound as a foam.
LC-MS: rt=0.95 min, 559 (M, ES+).

Example 18

2-[(2-Chloro-5-dimethylamino-phenyl)-(3,4-dimethoxy-benzenesulfonyl)-amino]-N-ethyl-N-(5-methyl-thiazol-2-ylmethyl)-acetamide prepared by reaction of [(2-chloro-5-dimethylamino-phenyl)-(3,4-dimethoxy-benzenesulfonyl)-amino]-acetic acid with.ethyl-(5-methyl-thiazol-2-ylmethyl)-amine
FC (EA) gave the title compound as a foam.
LC-MS: rt=0.95 min, 567 (M, ES+).

Example 19

2-[(2-Chloro-5-dimethylamino-phenyl)-(3,4-dimethoxy-benzenesulfonyl)-amino]-N-ethyl-N-(2-methyl-oxazol-4-ylmethyl)-acetamide prepared by reaction of [(2-chloro-5-dimethylamino-phenyl)-(3,4-dimethoxy-benzenesulfonyl)-amino]-acetic acid with.ethyl-(2-methyl-oxazol-4-ylmethyl)-amine
FC (EA) gave the title compound as a foam.
LC-MS: rt=0.95 min, 552 (M+1, ES+).

Example 20

2-[(6-Chloro-3-methyl-benzo[d]isothiazol-5-yl)-(3,4-dimethoxy-benzenesulfonyl)-amino]-N-ethyl-N-pyridin-2-ylmethyl-acetamide prepared by reaction of [(6-chloro-3-methyl-benzo[d]isothiazol-5-yl)-(3,4-dimethoxy-benzenesulfonyl)-amino]-acetic acid with ethyl-pyridin-2-ylmethyl-amine.
FC (DCM/MeOH: 99/1 to 93/7) gave the title compound as a foam.
LC-MS: rt=0.85 min, 575 (M+1, ES+).

Example 21

2-[(6-Chloro-3-methyl-benzo[d]isothiazol-5-yl)-(3,4-dimethoxy-benzenesulfonyl)-amino]-N-ethyl-N-(6-methyl-pyridin-2-ylmethyl)-acetamide prepared by reaction of [(6-chloro-3-methyl-benzo[d]isothiazol-5-yl)-(3,4-dimethoxy-benzenesulfonyl)-amino]-acetic acid with ethyl-(6-methyl-pyridin-2-ylmethyl)-amine.
FC (DCM/MeOH: 99/1 to 93/7) gave the title compound as a foam.
LC-MS: rt=0.83 min, 589 (M+1, ES+).

Example 22

2-[(6-Chloro-3-methyl-benzo[d]isothiazol-5-yl)-(3,4-dimethoxy-benzenesulfonyl)-amino]-N-ethyl-N-(3-methyl-pyridin-2-ylmethyl)-acetamide prepared by reaction of [(6-chloro-3-methyl-benzo[d]isothiazol-5-yl)-(3,4-dimethoxy-benzenesulfonyl)-amino]-acetic acid with ethyl-(3-methyl-pyridin-2-ylmethyl)-amine.
FC (DCM/MeOH: 99/1 to 93/7) gave the title compound as a foam.
LC-MS: rt=0.86 min, 589 (M+1, ES+).

Example 23

2-[(6-Chloro-3-methyl-benzo[d]isothiazol-5-yl)-(3,4-dimethoxy-benzenesulfonyl)-amino]-N-ethyl-N-(5-methyl-pyrazin-2-ylmethyl)-acetamide prepared by reaction of [(6-chloro-3-methyl-benzo[d]isothiazol-5-yl)-(3,4-dimethoxy-benzenesulfonyl)-amino]-acetic acid with ethyl-(5-methyl-pyrazin-2-ylmethyl)-amine.
FC (DCM/MeOH: 99/1 to 93/7) gave the title compound as a foam.
LC-MS: rt=0.97 min, 590 (M+1, ES+).

Example 24

2-[(6-Chloro-3-methyl-benzo[d]isothiazol-5-yl)-(3,4-dimethoxy-benzenesulfonyl)-amino]-N-ethyl-N-(6-methyl-pyrazin-2-ylmethyl)-acetamide prepared by reaction of [(6-chloro-3-methyl-benzo[d]isothiazol-5-yl)-(3,4-dimethoxy-benzenesulfonyl)-amino]-acetic acid with ethyl-(6-methyl-pyrazin-2-ylmethyl)-amine.
FC (DCM/MeOH: 99/1 to 93/7) gave the title compound as a foam.
LC-MS: rt=0.98 min, 590 (M+1, ES+).

Example 25

2-[(6-Chloro-3-methyl-benzo[d]isothiazol-5-yl)-(3,4-dimethoxy-benzenesulfonyl)-amino]-N-ethyl-N-(1-methyl-1H-pyrazol-3-ylmethyl)-acetamide prepared by reaction of [(6-chloro-3-methyl-benzo[d]isothiazol-5-yl)-(3,4-dimethoxy-benzenesulfonyl)-amino]-acetic acid with ethyl-(1-methyl-1H-pyrazol-3-ylmethyl)-amine.
FC (DCM/MeOH: 99/1 to 93/7) gave the title compound as a foam.
LC-MS: rt=0.97 min, 578 (M+1, ES+).

Example 26

2-[(6-Chloro-3-methyl-benzo[d]isothiazol-5-yl)-(3,4-dimethoxy-benzenesulfonyl)-amino]-N-ethyl-N-(1,5-dimethyl-1H-pyrazol-3-ylmethyl)-acetamide prepared by reaction of [(6-chloro-3-methyl-benzo[d]isothiazol-5-yl)-(3,4-dimethoxy-benzenesulfonyl)-amino]-acetic acid with ethyl-(1,5-dimethyl-1H-pyrazol-3-ylmethyl)-amine.
FC (DCM/MeOH: 99/1 to 93/7) gave the title compound as a foam.
LC-MS: rt=0.98 min, 592 (M, ES+).

Example 27

2-[(4-Chloro-2-cyano-phenyl)-(3,4-dimethoxy-benzenesulfonyl)-amino]-N,N-diethyl-acetamide prepared by reaction of N-(4-chloro-2-cyano-phenyl)-3,4-dimethoxy-benzenesulfonamide with 2-chloro-N,N-diethylacetamide as Example 1
FC (EA) gave the title compound as a foam.
LC-MS: rt=0.98 min. 466 (M, ES+).

Example 28

2-[(4-Chloro-2-cyano-phenyl)-(3,4-dimethoxy-benzenesulfonyl)-amino]-N-cyclopropyl-N-(6-methyl-pyridin-2-ylmethyl)-acetamide prepared by reaction of [(4-chloro-2-cyano-phenyl)-(3,4-dimethoxy-benzenesulfonyl)-amino]-acetic acid with cyclopropyl-(6-methyl-pyridin-2-ylmethyl)-amine
FC (DCM/MeOH: 99/1 to 93/7) gave the title compound as a foam.
LC-MS: rt=0.85 min, 555 (M, ES+).

Example 29

2-[(2-Chloro-5-dimethylamino-phenyl)-(3,4-dimethoxy-benzenesulfonyl)-amino]-N-ethyl-N-pyrazin-2-ylmethyl-acetamide prepared by reaction of [(2-chloro-5-dimethylamino-phenyl)-(3,4-dimethoxy-benzenesulfonyl)-amino]-acetic acid with ethyl-pyrazin-2-ylmethylamine.
FC (EA) gave the title compound as a foam.
LC-MS: rt=0.81 min, 548 (M, ES+).

Example 30

2-[(2-Chloro-5-dimethylamino-phenyl)-(3,4-dimethoxy-benzenesulfonyl)-amino]-N-ethyl-N-pyrimidin-5-ylmethyl-acetamide prepared by reaction of [(2-chloro-5-dimethylamino-phenyl)-(3,4-dimethoxy-benzenesulfonyl)-amino]-acetic acid with ethyl-pyrimidin-5-ylmethyl-amine
FC (EA) gave the title compound as a foam.
LC-MS: rt=0.87 min, 548 (M, ES+).

Example 31

2-[(2-Chloro-5-dimethylamino-phenyl)-(3,4-dimethoxy-benzenesulfonyl)-amino]-N-ethyl-N-thiazol-4-ylmethylamine-acetamide prepared by reaction of [(2-chloro-5-dimethylamino-phenyl)-(3,4-dimethoxy-benzenesulfonyl)-amino]-acetic acid with ethyl-thiazol-4-ylmethyl-amine
FC (EA) gave the title compound as a foam.
LC-MS: rt=0.85 min, 553 (M, ES+).

Example 32

2-[(2-Chloro-5-dimethylamino-phenyl)-(3,4-dimethoxy-benzenesulfonyl)-amino]-N-ethyl-N-(5-methyl-[1,3,4]thiadiazol-2-ylmethyl)-acetamide prepared by reaction of [(2-chloro-5-dimethylamino-phenyl)-(3,4-dimethoxy-benzenesulfonyl)-amino]-acetic acid with ethyl-(5-methyl-[1,3,4]thiadiazol-2-ylmethyl)-amine
FC (EA) gave the title compound as a foam.
LC-MS: rt=0.89 min, 568 (M, ES+).

Example 33

2-[(2-Chloro-5-dimethylamino-phenyl)-(3,4-dimethoxy-benzenesulfonyl)-amino]-N-ethyl-N-thiazol-2-ylmethyl-acetamide prepared by reaction of [(2-chloro-5-dimethylamino-phenyl)-(3,4-dimethoxy-benzenesulfonyl)-amino]-acetic acid with ethyl-thiazol-2-ylmethyl-amine
FC (EA) gave the title compound as a foam.
LC-MS: rt=0.87 min, 553 (M, ES+).

Example 34

2-[(2-Chloro-5-dimethylamino-phenyl)-(3,4-dimethoxy-benzenesulfonyl)-amino]-N-ethyl-N-(5-methyl-oxazol-2-ylmethyl)-acetamide prepared by reaction of [(2-chloro-5-dimethylamino-phenyl)-(3,4-dimethoxy-benzenesulfonyl)-amino]-acetic acid with ethyl-(5-methyl-oxazol-2-ylmethyl)-amine
FC (EA) gave the title compound as a foam.
LC-MS: rt=0.85 min, 551 (M, ES+).

Example 35

2-[(2-Chloro-5-dimethylamino-phenyl)-(3,4-dimethoxy-benzenesulfonyl)-amino]-N-ethyl-N-isoxazol-5-ylmethyl-acetamide prepared by reaction of [(2-chloro-5-dimethylamino-phenyl)-(3,4-dimethoxy-benzenesulfonyl)-amino]-acetic acid with ethyl-isoxazol-5-ylmethyl-amine
FC (EA) gave the title compound as a foam.
LC-MS: rt=0.86 min, 537 (M, ES+).

Example 36

2-[(2-Chloro-5-dimethylamino-phenyl)-(3,4-dimethoxy-benzenesulfonyl)-amino]-N-ethyl-N-thiazol-5-ylmethyl-acetamide prepared by reaction of [(2-chloro-5-dimethylamino-phenyl)-(3,4-dimethoxy-benzenesulfonyl)-amino]-acetic acid with ethyl-thiazol-5-ylmethyl-amine
FC (EA) gave the title compound as a foam.
LC-MS: rt=0.88 min, 553 (M, ES+).

Example 37

2-[(2-Chloro-5-dimethylamino-phenyl)-(3,4-dimethoxy-benzenesulfonyl)-amino]-N-ethyl-N-(3-fluoro-pyridin-2-ylmethyl)-acetamide prepared by reaction of [(2-chloro-5-dimethylamino-phenyl)-(3,4-dimethoxy-benzenesulfonyl)-amino]-acetic acid with ethyl-(3-fluoro-pyridin-2-ylmethyl)-amine
FC (EA) gave the title compound as a foam.
LC-MS: rt=0.82 min, 565 (M, ES+).

Example 38

2-[(2-Chloro-5-dimethylamino-phenyl)-(3,4-dimethoxy-benzenesulfonyl)-amino]-N-ethyl-N-(1-methyl-1H-pyrazol-4-ylmethyl)-acetamide prepared by reaction of [(2-chloro-5-dimethylamino-phenyl)-(3,4-dimethoxy-benzenesulfonyl)-amino]-acetic acid with ethyl-(1-methyl-1H-pyrazol-4-ylmethyl)-amine
FC (EA) gave the title compound as a foam.
LC-MS: rt=0.85 min, 550 (M, ES+).

Example 39

2-[(2-Chloro-5-dimethylamino-phenyl)-(3,4-dimethoxy-benzenesulfonyl)-amino]-N-ethyl-N-(1,5-dimethyl-1H-pyrazol-4-ylmethyl)-acetamide prepared by reaction of [(2-chloro-5-dimethylamino-phenyl)-(3,4-dimethoxy-benzenesulfonyl)-amino]-acetic acid with ethyl-(1,5-dimethyl-1H-pyrazol-4-ylmethyl)-amine
FC (EA) gave the title compound as a foam.
LC-MS: rt=0.87 min, 564 (M, ES+).

Example 40

2-[(2-Chloro-5-dimethylamino-phenyl)-(3,4-dimethoxy-benzenesulfonyl)-amino]-N-(4-chloro-1-methyl-1H-pyrazol-3-ylmethyl)-N-cyclopropyl-acetamide prepared by reaction of [(2-chloro-5-dimethylamino-phenyl)-(3,4-dimethoxy-benzenesulfonyl)-amino]-acetic acid with (4-chloro-1-methyl-1H-pyrazol-3-ylmethyl)-cyclopropyl-amine
FC (EA) gave the title compound as a foam.
LC-MS: rt=0.88 min, 596 (M, ES+).

Example 41

2-[(2-Chloro-5-dimethylamino-phenyl)-(3,4-dimethoxy-benzenesulfonyl)-amino]-N-cyclopropyl-(6-methoxy-3-methyl-pyridin-2-ylmethyl)-acetamide prepared by reaction of [(2-chloro-5-dimethylamino-phenyl)-(3,4-dimethoxy-benzenesulfonyl)-amino]-acetic acid with cyclopropyl-(6-methoxy-3-methyl-pyridin-2-ylmethyl)-amine
FC (EA) gave the title compound as a foam.
LC-MS: rt=0.85 min, 603 (M, ES+).

Example 42

2-[(2-Chloro-5-dimethylamino-phenyl)-(3,4-dimethoxy-benzenesulfonyl)-amino]-N-ethyl-(2-methyl-thiazol-5-ylmethyl)-acetamide prepared by reaction of [(2-chloro-5-dimethylamino-phenyl)-(3,4-dimethoxy-benzenesulfonyl)-amino]-acetic acid with ethyl-(2-methyl-thiazol-5-ylmethyl)-amine
FC (EA) gave the title compound as a foam.
LC-MS: rt=0.86 min, 567 (M, ES+).

Example 43

2-[(2-Chloro-5-dimethylamino-phenyl)-(3,4-dimethoxy-benzenesulfonyl)-amino]-N-ethyl-(2-methyl-pyrimidin-4-ylmethyl)-acetamide prepared by reaction of [(2-chloro-5-dimethylamino-phenyl)-(3,4-dimethoxy-benzenesulfonyl)-amino]-acetic acid with ethyl-(2-methyl-pyrimidin-4-ylmethyl)-amine
FC (EA) gave the title compound as a foam.
LC-MS: rt=0.85 min, 562 (M, ES+).

Example 44

2-[(2-Chloro-5-dimethylamino-phenyl)-(3,4-dimethoxy-benzenesulfonyl)-amino]-N-ethyl-(5-methyl-pyridin-3-ylmethyl)-acetamide prepared by reaction of [(2-chloro-5-dimethylamino-phenyl)-(3,4-dimethoxy-benzenesulfonyl)-amino]-acetic acid with ethyl-(5-methyl-pyridin-3-ylmethyl)-amine
FC (EA) gave the title compound as a foam.
LC-MS: rt=0.76 min, 561 (M, ES+).

Example 45

2-[(2-Chloro-5-dimethylamino-phenyl)-(3,4-dimethoxy-benzenesulfonyl)-amino]-N-ethyl-(4-methyl-pyridin-2-ylmethyl)-acetamide prepared by reaction of [(2-chloro-5-dimethylamino-phenyl)-(3,4-dimethoxy-benzenesulfonyl)-amino]-acetic acid with ethyl-(4-methyl-pyridin-2-ylmethyl)-amine
FC (EA) gave the title compound as a foam.
LC-MS: rt=0.78 min, 561 (M, ES+).

Example 46

2-[(2-Chloro-5-dimethylamino-phenyl)-(3,4-dimethoxy-benzenesulfonyl)-amino]-N-ethyl-N-pyridin-3-ylmethyl)-acetamide prepared by reaction of [(2-chloro-5-dimethylamino-phenyl)-(3,4-dimethoxy-benzenesulfonyl)-amino]-acetic acid with ethyl-pyridin-3-ylmethyl)-amine
FC (EA) gave the title compound as a foam.
LC-MS: rt=0.77 min, 547 (M, ES+).

Example 47

2-[(2-Chloro-5-dimethylamino-phenyl)-(3,4-dimethoxy-benzenesulfonyl)-amino]-N-ethyl-N-(1,4-dimethyl-1H-pyrazol-3-ylmethyl)-acetamide prepared by reaction of [(2-chloro-5-dimethylamino-phenyl)-(3,4-dimethoxy-benzenesulfonyl)-amino]-acetic acid with ethyl-(1,4-dimethyl-1H-pyrazol-3-ylmethyl)-amine
FC (EA) gave the title compound as a foam.
LC-MS: rt=0.82 min. 564 (M, ES+).

Example 48

2-[(2-Chloro-5-dimethylamino-phenyl)-(3,4-dimethoxy-benzenesulfonyl)-amino]-N-ethyl-N-(3-methyl-isoxazol-5-ylmethyl)-acetamide prepared by reaction of [(2-chloro-5-dimethylamino-phenyl)-(3,4-dimethoxy-benzenesulfonyl)-amino]-acetic acid with ethyl-(3-methyl-isoxazol-5-ylmethyl)-amine
FC (EA) gave the title compound as a foam.
LC-MS: rt=0.85 min, 551 (M, ES+).

Example 49

2-[(2-Chloro-5-dimethylamino-phenyl)-(3,4-dimethoxy-benzenesulfonyl)-amino]-N-ethyl-N-isoxazol-3-ylmethyl-acetamide prepared by reaction of [(2-chloro-5-dimethylamino-phenyl)-(3,4-dimethoxy-benzenesulfonyl)-amino]-acetic acid with ethyl-isoxazol-3-ylmethyl-amine
FC (EA) gave the title compound as a foam.
LC-MS: rt=0.85 min, 537 (M, ES+).

Example 50

2-[(2-Chloro-5-dimethylamino-phenyl)-(3,4-dimethoxy-benzenesulfonyl)-amino]-N-ethyl-N-(3-methyl-isothiazol-5-ylmethyl)-acetamide prepared by reaction of [(2-chloro-5-dimethylamino-phenyl)-(3,4-dimethoxy-benzenesulfonyl)-amino]-acetic acid with ethyl-(3-methyl-isothiazol-5-ylmethyl)-amine
FC (EA) gave the title compound as a foam.
LC-MS: rt=0.87 min, 567 (M, ES+).

Example 51

2-[(2-Chloro-5-dimethylamino-phenyl)-(3,4-dimethoxy-benzenesulfonyl)-amino]-N-ethyl-N-isothiazol-5-ylmethyl-acetamide prepared by reaction of [(2-chloro-5-dimethylamino-phenyl)-(3,4-dimethoxy-benzenesulfonyl)-amino]-acetic acid with ethyl-isothiazol-5-ylmethyl-amine
FC (EA) gave the title compound as a foam.
LC-MS: rt=0.86 min, 553 (M, ES+).

Example 52

2-[(2-Chloro-5-dimethylamino-phenyl)-(3,4-dimethoxy-benzenesulfonyl)-amino]-N-ethyl-N-isothiazol-3-ylmethyl-acetamide prepared by reaction of [(2-chloro-5-dimethylamino-phenyl)-(3,4-dimethoxy-benzenesulfonyl)-amino]-acetic acid with ethyl-isothiazol-3-ylmethyl-amine
FC (EA) gave the title compound as a foam.
LC-MS: rt=0.85 min, 553 (M, ES+).

Example 53

2-[(2-Chloro-5-dimethylamino-phenyl)-(3,4-dimethoxy-benzenesulfonyl)-amino]-N-ethyl-N-(4-methyl-isoxazol-5-ylmethyl)-acetamide prepared by reaction of [(2-chloro-5-dimethylamino-phenyl)-(3,4-dimethoxy-benzenesulfonyl)-amino]-acetic acid with ethyl-(3-methyl-isoxazol-5-ylmethyl)-amine
FC (EA) gave the title compound as a foam.
LC-MS: rt=0.85 min, 551 (M, ES+).

Example 54

2-[(2-Chloro-5-dimethylamino-phenyl)-(3,4-dimethoxy-benzenesulfonyl)-amino]-N-ethyl-N-(6-trifluoromethyl-pyridin-2-ylmethyl)-acetamide prepared by reaction of [(2-chloro-5-dimethylamino-phenyl)-(3,4-dimethoxy-benzenesulfonyl)-amino]-acetic acid with ethyl-(6-trifluoromethyl-pyridin-2-ylmethyl)-amine
FC (EA) gave the title compound as a foam.
LC-MS: rt=0.88 min, 615 (M, ES+).

Example 55

2-[(2-Chloro-5-dimethylamino-phenyl)-(3,4-dimethoxy-benzenesulfonyl)-amino]-N-(2-hydroxyethyl)-N-pyridin-2-ylmethyl-acetamide prepared by reaction of [(2-chloro-5-dimethylamino-phenyl)-(3,4-dimethoxy-benzenesulfonyl)-amino]-acetic acid with. 2-[(pyridin-2-ylmethyl)-amino]-ethanol.
FC (DCM/MeOH:99/1 to 93/7) gave the title compound as a foam.
LC-MS: rt=0.73 min, 563 (M, ES+).

Example 56

2-[(2-Chloro-5-dimethylamino-phenyl)-(3,4-dimethoxy-benzenesulfonyl)-amino]-N-ethyl)-N-(5-methyl-isoxazol-3-ylmethyl)-acetamide prepared by reaction of [(2-chloro-5-dimethylamino-phenyl)-(3,4-dimethoxy-benzenesulfonyl)-amino]-acetic acid with. ethyl-(5-methyl-isoxazol-3-ylmethyl)-amine
FC (EA) gave the title compound as a foam.
LC-MS: rt=0.83 min, 551 (M, ES+).

Example 57

2-[(2-Chloro-5-dimethylamino-phenyl)-(3,4-dimethoxy-benzenesulfonyl)-amino]-N,N-diethyl-acetamide prepared by reaction of N-(2-chloro-5-dimethylamino-phenyl)-3,4-dimethoxy-benzenesulfonamide with 2-chloro-N,N-diethylacetamide as Example 1
FC (EA) gave the title compound as a foam.
LC-MS: rt=0.95 min, 484 (M, ES+).

Example 58

2-[(2-Cyano-5-dimethylamino-phenyl)-(3,4-dimethoxy-benzenesulfonyl)-amino]-N,N-diethyl-acetamide prepared by reaction of N-(2-cyano-5-dimethylamino-phenyl)-3,4-dimethoxy-benzenesulfonamide with 2-chloro-N,N-diethylacetamide as Example 1
FC (EA) gave the title compound as a foam.
LC-MS: rt=0.97 min, 474 (M, ES+).

Example 59

2-[(2-Chloro-5-dimethylamino-phenyl)-(3,4-dimethoxy-benzenesulfonyl)-amino]-N-ethyl-N-(6-methoxy-pyridin-2-ylmethyl)-acetamide prepared by reaction of N-(2-chloro-5-dimethylamino-phenyl)-3,4-dimethoxy-benzenesulfonamide with ethyl-(6-methoxy-pyridin-2-ylmethyl)-amine
FC (EA) gave the title compound as a foam.
LC-MS: rt=0.87 min, 577 (M, ES+).

Example 60

2-[(3,4-dimethoxy-benzenesulfonyl)-(5-dimethylamino-2-fluoro-phenyl)-amino]-N-ethyl-N-pyridin-2-ylmethyl-acetamide prepared by reaction of [(3,4-dimethoxy-benzenesulfonyl)-(5-dimethylamino-2-fluoro-phenyl)-amino]-acetic acid.with ethyl-pyridin-2-ylmethyl-amine
FC (DCM/MeOH: 99/1 to 93/7) gave the title compound as a foam.
LC-MS: rt=0.87 min, 530 (M, ES+).

II. Biological Assays
In Vitro Assay
The orexin receptor antagonistic activity of the compounds of formula (I) is determined in accordance with the following experimental method.

Experimental Method

Intracellular Calcium Measurements:
Chinese hamster ovary (CHO) cells expressing the human orexin-1 receptor and the human orexin-2 receptor, respectively, are grown in culture medium (Ham F-12 with L-Glutamine) containing 300 µg/ml G418, 100 U/ml penicillin, 100 µg/ml streptomycin and 10% inactivated fetal calf serum (FCS). The cells are seeded at 80,000 cells/well into 96-well black clear bottom sterile plates (Costar) which have been precoated with 1% gelatine in Hanks' Balanced Salt Solution (HBSS). All reagents are from Gibco BRL. The seeded plates are incubated overnight at 37° C. in 5% $CO_2$.

Human orexin-A as an agonist is prepared as 1 mM stock solution in methanol:water (1:1), diluted in HBSS containing 0.1% bovine serum albumin (BSA) and 2 mM HEPES for use in the assay at a final concentration of 10 nM.

Antagonists are prepared as 10 mM stock solution in DMSO, then diluted in 96-well plates, first in DMSO, then in HBSS containing 0.1% bovine serum albumin (BSA) and 2 mM HEPES.

On the day of the assay, 100 µl of loading medium (HBSS containing 1% FCS, 2 mM HEPES, 5 mM probenecid (Sigma) and 3 µM of the fluorescent calcium indicator fluo-3 AM (1 mM stock solution in DMSO with 10% pluronic acid) (Molecular Probes) is added to each well.

The 96-well plates are incubated for 60 min at 37° C. in 5% $CO_2$. The loading solution is then aspirated and cells are washed 3 times with 200 µl HBSS containing 2.5 mM probenecid, 0.1% BSA, 2 mM HEPES. 100 µl of that same buffer is left in each well.

Within the Fluorescent Imaging Plate Reader (FLIPR, Molecular Devices), antagonists are added to the plate in a volume of 50 µl, incubated for 20 min and finally 100 µl of agonist is added. Fluorescence is measured for each well at 1 second intervals, and the height of each fluorescence peak is compared to the height of the fluorescence peak induced by 10 nM orexin-A with buffer in place of antagonist. For each antagonist, $IC_{50}$ value (the concentration of compound needed to inhibit 50% of the agonistic response) is determined. Antagonistic activities of compounds are in the nanomolar range with respect to $OX_1$ and $OX_2$ receptors. Selected compounds are displayed in Table I.

TABLE 1

| Compound | OX$_1$ IC$_{50}$ (nM) | OX$_2$ IC$_{50}$ (nM) |
| --- | --- | --- |
| Example 11 | 6 | 4 |
| Example 14 | 15 | 12 |
| Example 21 | 8 | 7 |
| Example 27 | 180 | 2 |
| Example 55 | 63 | 7 |
| Example 58 | 166 | 10 |

The invention claimed is:

1. A compound of formula (I)

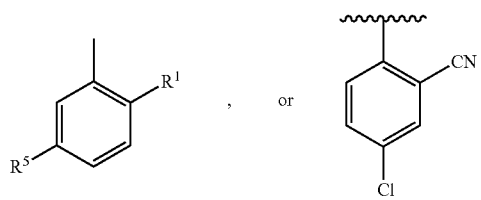

wherein
A represents

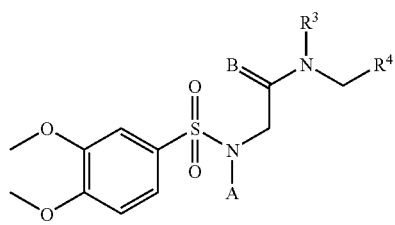

B represents O or S;
R$^1$ represents halogen or cyano;
R$^3$ represents (C$_{1-4}$)alkyl, (C$_{3-6}$)cycloalkyl or hydroxy (C$_{1-4}$)alkyl;
R$^4$ represents (C$_{1-4}$)alkyl or an unsubstituted, monosubstituted or di-substituted five- or six-membered heteroaryl wherein the substituents are independently selected from the group consisting of halogen, (C$_{1-4}$)alkyl, (C$_{1-4}$)alkoxy, trifluoromethyl, difluoromethoxy and trifluoromethoxy;
R$^5$ represents N(CH$_3$)$_2$, or isopropenyl;
or a pharmaceutically acceptable salt thereof.

2. A compound according to claim 1, wherein B represents O;
or a pharmaceutically acceptable salt thereof.

3. A compound according to claim 1, wherein R$^1$ represents chlorine;
or a pharmaceutically acceptable salt thereof.

4. A compound according to claim 1, wherein R$^4$ represents an unsubstituted, monosubstituted or di-substituted five- or six-membered heteroaryl, substituted with halogen, (C$_{1-4}$) alkyl, (C$_{1-4}$)alkoxy, trifluoromethyl, difluoromethoxy, or trifluoromethoxy;
or a pharmaceutically acceptable salt thereof.

5. A compound according to claim 1, wherein
R$^5$ represents N(CH$_3$)$_2$;
or a pharmaceutically acceptable salt thereof.

6. A compound according to claim 1 selected from the group consisting of:

2-[(2-Chloro-5-dimethylamino-phenyl)-(3,4-dimethoxy-benzenesulfonyl)-amino]-N-ethyl-N-pyridin-2-ylmethyl-acetamide;
2-[(2-Chloro-5-dimethylamino-phenyl)-(3,4-dimethoxy-benzenesulfonyl)-amino]-N-ethyl-N-(6-methyl-pyridin-2-ylmethyl)-acetamide;
2-[(3,4-dimethoxy-benzenesulfonyl)-(5-dimethylamino-2-fluoro-phenyl)-amino]-N-ethyl-N-(6-methyl-pyridin-2-ylmethyl)-acetamide;
2-[(2-Chloro-5-dimethylamino-phenyl)-(3,4-dimethoxy-benzenesulfonyl)-amino]-N-ethyl-N-(6-methyl-pyridin-2-ylmethyl)-acetamide;
2-[(2-Chloro-5-dimethylamino-phenyl)-(3,4-dimethoxy-benzenesulfonyl)-amino]-N-ethyl-N-(6-methyl-pyrazin-2-ylmethyl)-acetamide;
2-[(2-Chloro-5-dimethylamino-phenyl)-(3,4-dimethoxy-benzenesulfonyl)-amino]-N-ethyl-N-(5-methyl-pyrazin-2-ylmethyl)-acetamide;
2-[(2-Chloro-5-dimethylamino-phenyl)-(3,4-dimethoxy-benzenesulfonyl)-amino]-N-ethyl-N-(3-methyl-pyridin-2-ylmethyl)-acetamide;
2-[(2-Chloro-5-dimethylamino-phenyl)-(3,4-dimethoxy-benzenesulfonyl)-amino]-N-ethyl-N-(1-methyl-1H-pyrazol-3-ylmethyl)-acetamide;
2-[(2-Chloro-5-dimethylamino-phenyl)-(3,4-dimethoxy-benzenesulfonyl)-amino]-N-ethyl-N-(1,5-dimethyl-1H-pyrazol-3-ylmethyl)-acetamide;
2-[(4-Chloro-2-cyano-phenyl)-(3,4-dimethoxy-benzenesulfonyl)-amino]-N-ethyl-N-(6-methyl-pyridin-2-ylmethyl)-acetamide;
2-[(2-Chloro-5-dimethylamino-phenyl)-(3,4-dimethoxy-benzenesulfonyl)-amino]-N-(2-hydroxy-ethyl)-N-(6-methyl-pyridin-2ylmethyl)-acetamide;
2-[(2-Chloro-5-dimethylamino-phenyl)-(3,4-dimethoxy-benzenesulfonyl)-amino]-N-ethyl-N-(6-methyl-pyrazin-2-ylmethyl)-thioacetamide;
2-[(2-Chloro-5-isopropenyl-phenyl)-(3,4-dimethoxy-benzenesulfonyl)-amino]-N,N-diethyl-acetamide;
2-[(2-Chloro-5-dimethylamino-phenyl)-(3,4-dimethoxy-benzenesulfonyl)-amino]-N-cyclopropyl-N-(6-methyl-pyridin-2-ylmethyl)-acetamide;
2-[(2-Chloro-5-dimethylamino-phenyl)-(3,4-dimethoxy-benzenesulfonyl)-amino]-N-cyclopropyl-N-(6-methoxy-pyridin-2-ylmethyl)-acetamide;
2-[(2-Chloro-5-dimethylamino-phenyl)-(3,4-dimethoxy-benzenesulfonyl)-amino]-N-cyclopropyl-N-pyridin-2-ylmethyl-acetamide;
2-[(2-Chloro-5-dimethylamino-phenyl)-(3,4-dimethoxy-benzenesulfonyl)-amino]-N-ethyl-N-(5-methyl-thiazol-2-ylmethyl)-acetamide;
2-[(2-Chloro-5-dimethylamino-phenyl)-(3,4-dimethoxy-benzenesulfonyl)-amino]-N-ethyl-N-(2-methyl-oxazol-4-ylmethyl)-acetamide;
2-[(4-Chloro-2-cyano-phenyl)-(3,4-dimethoxy-benzenesulfonyl)-amino]-N,N-diethyl-acetamide;
2-[(4-Chloro-2-cyano-phenyl)-(3,4-dimethoxy-benzenesulfonyl)-amino]-N-cyclopropyl-N-(6-methyl-pyridin-2-ylmethyl)-acetamide;
2-[(2-Chloro-5-dimethylamino-phenyl)-(3,4-dimethoxy-benzenesulfonyl)-amino]-N-ethyl-N-pyrazin-2-ylmethyl-acetamide;
2-[(2-Chloro-5-dimethylamino-phenyl)-(3,4-dimethoxy-benzenesulfonyl)-amino]-N-ethyl-N-pyrimidin-5-ylmethyl-acetamide;
2-[(2-Chloro-5-dimethylamino-phenyl)-(3,4-dimethoxy-benzenesulfonyl)-amino]-N-ethyl-N-thiazol-4-ylmethylamine-acetamide;

2-[(2-Chloro-5-dimethylamino-phenyl)-(3,4-dimethoxy-benzenesulfonyl)-amino]-N-ethyl-N-(5-methyl-[1,3,4]thiadiazol-2-ylmethyl)-acetamide;

2-[(2-Chloro-5-dimethylamino-phenyl)-(3,4-dimethoxy-benzenesulfonyl)-amino]-N-ethyl-N-thiazol-2-ylmethyl-acetamide;

2-[(2-Chloro-5-dimethylamino-phenyl)-(3,4-dimethoxy-benzenesulfonyl)-amino]-N-ethyl-N-(5-methyl-oxazol-2-ylmethyl)-acetamide;

2-[(2-Chloro-5-dimethylamino-phenyl)-(3,4-dimethoxy-benzenesulfonyl)-amino]-N-ethyl-N-isoxazol-5-ylmethyl-acetamide;

2-[(2-Chloro-5-dimethylamino-phenyl)-(3,4-dimethoxy-benzenesulfonyl)-amino]-N-ethyl-N-thiazol-5-ylmethyl-acetamide;

2-[(2-Chloro-5-dimethylamino-phenyl)-(3,4-dimethoxy-benzenesulfonyl)-amino]-N-ethyl-N-(3-fluoro-pyridin-2-ylmethyl)-acetamide;

2-[(2-Chloro-5-dimethylamino-phenyl)-(3,4-dimethoxy-benzenesulfonyl)-amino]-N-ethyl-N-(1-methyl-1H-pyrazol-4-ylmethyl)-acetamide;

2-[(2-Chloro-5-dimethylamino-phenyl)-(3,4-dimethoxy-benzenesulfonyl)-amino]-N-ethyl-N-(1,5-dimethyl-1H-pyrazol-4-ylmethyl)-acetamide;

2-[(2-Chloro-5-dimethylamino-phenyl)-(3,4-dimethoxy-benzenesulfonyl)-amino]-N-(4-chloro-1-methyl-1H-pyrazol-3-ylmethyl)-N-cyclopropyl-acetamide;

2-[(2-Chloro-5-dimethylamino-phenyl)-(3,4-dimethoxy-benzenesulfonyl)-amino]-N-cyclopropyl-(6-methoxy-3-methyl-pyridin-2-ylmethyl)-acetamide;

2-[(2-Chloro-5-dimethylamino-phenyl)-(3,4-dimethoxy-benzenesulfonyl)-amino]-N-ethyl-(2-methyl-thiazol-5-ylmethyl)-acetamide;

2-[(2-Chloro-5-dimethylamino-phenyl)-(3,4-dimethoxy-benzenesulfonyl)-amino]-N-ethyl-(2-methyl-pyrimidin-4-ylmethyl)-acetamide;

2-[(2-Chloro-5-dimethylamino-phenyl)-(3,4-dimethoxy-benzenesulfonyl)-amino]-N-ethyl-(5-methyl-pyridin-3-ylmethyl)-acetamide;

2-[(2-Chloro-5-dimethylamino-phenyl)-(3,4-dimethoxy-benzenesulfonyl)-amino]-N-ethyl-(4-methyl-pyridin-2-ylmethyl)-acetamide;

2-[(2-Chloro-5-dimethylamino-phenyl)-(3,4-dimethoxy-benzenesulfonyl)-amino]-N-ethyl-N-pyridin-3-ylmethyl)-acetamide;

2-[(2-Chloro-5-dimethylamino-phenyl)-(3,4-dimethoxy-benzenesulfonyl)-amino]-N-ethyl-N-(1,4-dimethyl-1H-pyrazol-3-ylmethyl)-acetamide;

2-[(2-Chloro-5-dimethylamino-phenyl)-(3,4-dimethoxy-benzenesulfonyl)-amino]-N-ethyl-N-(3-methyl-isoxazol-5-ylmethyl)-acetamide;

2-[(2-Chloro-5-dimethylamino-phenyl)-(3,4-dimethoxy-benzenesulfonyl)-amino]-N-ethyl-N-isoxazol-3-ylmethyl-acetamide;

2-[(2-Chloro-5-dimethylamino-phenyl)-(3,4-dimethoxy-benzenesulfonyl)-amino]-N-ethyl-N-(3-methyl-isothiazol-5-ylmethyl)-acetamide;

2-[(2-Chloro-5-dimethylamino-phenyl)-(3,4-dimethoxy-benzenesulfonyl)-amino]-N-ethyl-N-isothiazol-5-ylmethyl-acetamide;

2-[(2-Chloro-5-dimethylamino-phenyl)-(3,4-dimethoxy-benzenesulfonyl)-amino]-N-ethyl-N-isothiazol-3-ylmethyl-acetamide;

2-[(2-Chloro-5-dimethylamino-phenyl)-(3,4-dimethoxy-benzenesulfonyl)-amino]-N-ethyl-N-(4-methyl-isoxazol-5-ylmethyl)-acetamide;

2-[(2-Chloro-5-dimethylamino-phenyl)-(3,4-dimethoxy-benzenesulfonyl)-amino]-N-ethyl-N-(6-trifluoromethyl-pyridin-2-ylmethyl)-acetamide;

2-[(2-Chloro-5-dimethylamino-phenyl)-(3,4-dimethoxy-benzenesulfonyl)-amino]-N-(2-hydroxy-ethyl)-N-pyridin-2-ylmethyl-acetamide;

2-[(2-Chloro-5-dimethylamino-phenyl)-(3,4-dimethoxy-benzenesulfonyl)-amino]-N-ethyl-N-(5-methyl-isoxazol-3-ylmethyl)-acetamide;

2-[(2-Chloro-5-dimethylamino-phenyl)-(3,4-dimethoxy-benzenesulfonyl)-amino]-N,N-diethyl-acetamide;

2-[(2-Cyano-5-dimethylamino-phenyl)-(3,4-dimethoxy-benzenesulfonyl)-amino]-N,N-diethyl-acetamide;

2-[(2-Chloro-5-dimethylamino-phenyl)-(3,4-dimethoxy-benzenesulfonyl)-amino]-N-ethyl-N-(6-methoxy-pyridin-2-ylmethyl)-acetamide; and 2-[(3,4-dimethoxy-benzenesulfonyl)-(5-dimethylamino-2-fluoro-phenyl)-amino]-N-ethyl-N-pyridin-2-ylmethyl-acetamide;

or a pharmaceutically acceptable salt thereof.

7. The compound according to claim 1, wherein said compound is 2-[(2-Chloro-5-dimethylamino-phenyl)-(3,4-dimethoxy-benzenesulfonyl)-amino]-N-ethyl-N-(1,5-dimethyl-1H-pyrazol-3-ylmethyl)-acetamide;

or a pharmaceutically acceptable salt thereof.

8. The compound according to claim 1, wherein said compound is 2-[(2-Chloro-5-dimethylamino-phenyl)-(3,4-dimethoxy-benzenesulfonyl)-amino]-N-ethyl-N-(6-methyl-pyrazin-2-ylmethyl)-thioacetamide;

or a pharmaceutically acceptable salt thereof.

9. A pharmaceutical composition comprising a compound according to claim 1 and a pharmaceutically acceptable carrier.

10. The pharmaceutical composition according to claim 9, wherein said compound is selected from the group consisting of:

2-[(2-Chloro-5-dimethylamino-phenyl)-(3,4-dimethoxy-benzenesulfonyl)-amino]-N-ethyl-N-pyridin-2-ylmethyl-acetamide;

2-[(2-Chloro-5-dimethylamino-phenyl)-(3,4-dimethoxy-benzenesulfonyl)-amino]-N-ethyl-N-(6-methyl-pyridin-2-ylmethyl)-acetamide;

2-[(3,4-dimethoxy-benzenesulfonyl)-(5-dimethylamino-2-fluoro-phenyl)-amino]-N-ethyl-N-(6-methyl-pyridin-2-ylmethyl)-acetamide;

2-[(2-Chloro-5-dimethylamino-phenyl)-(3,4-dimethoxy-benzenesulfonyl)-amino]-N-ethyl-N-(6-methyl-pyridin-2-ylmethyl)-acetamide;

2-[(2-Chloro-5-dimethylamino-phenyl)-(3,4-dimethoxy-benzenesulfonyl)-amino]-N-ethyl-N-(6-methyl-pyrazin-2-ylmethyl)-acetamide;

2-[(2-Chloro-5-dimethylamino-phenyl)-(3,4-dimethoxy-benzenesulfonyl)-amino]-N-ethyl-N-(5-methyl-pyrazin-2-ylmethyl)-acetamide;

2-[(2-Chloro-5-dimethylamino-phenyl)-(3,4-dimethoxy-benzenesulfonyl)-amino]-N-ethyl-N-(3-methyl-pyridin-2-ylmethyl)-acetamide;

2-[(2-Chloro-5-dimethylamino-phenyl)-(3,4-dimethoxy-benzenesulfonyl)-amino]-N-ethyl-N-(1-methyl-1H-pyrazol-3-ylmethyl)-acetamide;

2-[(2-Chloro-5-dimethylamino-phenyl)-(3,4-dimethoxy-benzenesulfonyl)-amino]-N-ethyl-N-(1,5-dimethyl-1H-pyrazol-3-ylmethyl)-acetamide;

2-[(4-Chloro-2-cyano-phenyl)-(3,4-dimethoxy-benzenesulfonyl)-amino]-N-ethyl-N-(6-methyl-pyridin-2-ylmethyl)-acetamide;

2-[(2-Chloro-5-dimethylamino-phenyl)-(3,4-dimethoxy-benzenesulfonyl)-amino]-N-(2-hydroxy-ethyl)-N-(6-methyl-pyridin-2ylmethyl)-acetamide;

2-[(2-Chloro-5-dimethylamino-phenyl)-(3,4-dimethoxy-benzenesulfonyl)-amino]-N-ethyl-N-(6-methyl-pyrazin-2-ylmethyl)-thioacetamide;

2-[(2-Chloro-5-isopropenyl-phenyl)-(3,4-dimethoxy-benzenesulfonyl)-amino]-N,N-diethyl-acetamide;

2-[(2-Chloro-5-dimethylamino-phenyl)-(3,4-dimethoxy-benzenesulfonyl)-amino]-N-cyclopropyl-N-(6-methyl-pyridin-2-ylmethyl)-acetamide;

2-[(2-Chloro-5-dimethylamino-phenyl)-(3,4-dimethoxy-benzenesulfonyl)-amino]-N-cyclopropyl-N-(6-methoxy-pyridin-2-ylmethyl)-acetamide;

2-[(2-Chloro-5-dimethylamino-phenyl)-(3,4-dimethoxy-benzenesulfonyl)-amino]-N-cyclopropyl-N-pyridin-2-ylmethyl-acetamide;

2-[(2-Chloro-5-dimethylamino-phenyl)-(3,4-dimethoxy-benzenesulfonyl)-amino]-N-ethyl-N-(5-methyl-thiazol-2-ylmethyl)-acetamide;

2-[(2-Chloro-5-dimethylamino-phenyl)-(3,4-dimethoxy-benzenesulfonyl)-amino]-N-ethyl-N-(2-methyl-oxazol-4-ylmethyl)-acetamide;

2-[(4-Chloro-2-cyano-phenyl)-(3,4-dimethoxy-benzenesulfonyl)-amino]-N,N-diethyl-acetamide;

2-[(4-Chloro-2-cyano-phenyl)-(3,4-dimethoxy-benzenesulfonyl)-amino]-N-cyclopropyl-N-(6-methyl-pyridin-2-ylmethyl)-acetamide;

2-[(2-Chloro-5-dimethylamino-phenyl)-(3,4-dimethoxy-benzenesulfonyl)-amino]-N-ethyl-N-pyrazin-2-ylmethyl-acetamide;

2-[(2-Chloro-5-dimethylamino-phenyl)-(3,4-dimethoxy-benzenesulfonyl)-amino]-N-ethyl-N-pyrimidin-5-ylmethyl-acetamide;

2-[(2-Chloro-5-dimethylamino-phenyl)-(3,4-dimethoxy-benzenesulfonyl)-amino]-N-ethyl-N-thiazol-4-ylmethylamine-acetamide;

2-[(2-Chloro-5-dimethylamino-phenyl)-(3,4-dimethoxy-benzenesulfonyl)-amino]-N-ethyl-N-(5-methyl-[1,3,4]thiadiazol-2-ylmethyl)-acetamide;

2-[(2-Chloro-5-dimethylamino-phenyl)-(3,4-dimethoxy-benzenesulfonyl)-amino]-N-ethyl-N-thiazol-2-ylmethyl-acetamide;

2-[(2-Chloro-5-dimethylamino-phenyl)-(3,4-dimethoxy-benzenesulfonyl)-amino]-N-ethyl-N-(5-methyl-oxazol-2-ylmethyl)-acetamide;

2-[(2-Chloro-5-dimethylamino-phenyl)-(3,4-dimethoxy-benzenesulfonyl)-amino]-N-ethyl-N-isoxazol-5-ylmethyl-acetamide;

2-[(2-Chloro-5-dimethylamino-phenyl)-(3,4-dimethoxy-benzenesulfonyl)-amino]-N-ethyl-N-thiazol-5-ylmethyl-acetamide;

2-[(2-Chloro-5-dimethylamino-phenyl)-(3,4-dimethoxy-benzenesulfonyl)-amino]-N-ethyl-N-(3-fluoro-pyridin-2-ylmethyl)-acetamide;

2-[(2-Chloro-5-dimethylamino-phenyl)-(3,4-dimethoxy-benzenesulfonyl)-amino]-N-ethyl-N-(1-methyl-1H-pyrazol-4-ylmethyl)-acetamide;

2-[(2-Chloro-5-dimethylamino-phenyl)-(3,4-dimethoxy-benzenesulfonyl)-amino]-N-ethyl-N-(1,5-dimethyl-1H-pyrazol-4-ylmethyl)-acetamide;

2-[(2-Chloro-5-dimethylamino-phenyl)-(3,4-dimethoxy-benzenesulfonyl)-amino]-N-(4-chloro-1-methyl-1H-pyrazol-3-ylmethyl)-N-cyclopropyl-acetamide;

2-[(2-Chloro-5-dimethylamino-phenyl)-(3,4-dimethoxy-benzenesulfonyl)-amino]-N-cyclopropyl-(6-methoxy-3-methyl-pyridin-2-ylmethyl)-acetamide;

2-[(2-Chloro-5-dimethylamino-phenyl)-(3,4-dimethoxy-benzenesulfonyl)-amino]-N-ethyl-(2-methyl-thiazol-5-ylmethyl)-acetamide;

2-[(2-Chloro-5-dimethylamino-phenyl)-(3,4-dimethoxy-benzenesulfonyl)-amino]-N-ethyl-(2-methyl-pyrimidin-4-ylmethyl)-acetamide;

2-[(2-Chloro-5-dimethylamino-phenyl)-(3,4-dimethoxy-benzenesulfonyl)-amino]-N-ethyl-(5-methyl-pyridin-3-ylmethyl)-acetamide;

2-[(2-Chloro-5-dimethylamino-phenyl)-(3,4-dimethoxy-benzenesulfonyl)-amino]-N-ethyl-(4-methyl-pyridin-2-ylmethyl)-acetamide;

2-[(2-Chloro-5-dimethylamino-phenyl)-(3,4-dimethoxy-benzenesulfonyl)-amino]-N-ethyl-N-pyridin-3-ylmethyl)-acetamide;

2-[(2-Chloro-5-dimethylamino-phenyl)-(3,4-dimethoxy-benzenesulfonyl)-amino]-N-ethyl-N-(1,4-dimethyl-1H-pyrazol-3-ylmethyl)-acetamide;

2-[(2-Chloro-5-dimethylamino-phenyl)-(3,4-dimethoxy-benzenesulfonyl)-amino]-N-ethyl-N-(3-methyl-isoxazol-5-ylmethyl)-acetamide;

2-[(2-Chloro-5-dimethylamino-phenyl)-(3,4-dimethoxy-benzenesulfonyl)-amino]-N-ethyl-N-isoxazol-3-ylmethyl-acetamide;

2-[(2-Chloro-5-dimethylamino-phenyl)-(3,4-dimethoxy-benzenesulfonyl)-amino]-N-ethyl-N-(3-methyl-isothiazol-5-ylmethyl)-acetamide;

2-[(2-Chloro-5-dimethylamino-phenyl)-(3,4-dimethoxy-benzenesulfonyl)-amino]-N-ethyl-N-isothiazol-5-ylmethyl-acetamide;

2-[(2-Chloro-5-dimethylamino-phenyl)-(3,4-dimethoxy-benzenesulfonyl)-amino]-N-ethyl-N-isothiazol-3-ylmethyl-acetamide;

2-[(2-Chloro-5-dimethylamino-phenyl)-(3,4-dimethoxy-benzenesulfonyl)-amino]-N-ethyl-N-(4-methyl-isoxazol-5-ylmethyl)-acetamide;

2-[(2-Chloro-5-dimethylamino-phenyl)-(3,4-dimethoxy-benzenesulfonyl)-amino]-N-ethyl-N-(6-trifluoromethyl-pyridin-2-ylmethyl)-acetamide;

2-[(2-Chloro-5-dimethylamino-phenyl)-(3,4-dimethoxy-benzenesulfonyl)-amino]-N-(2-hydroxy-ethyl)-N-pyridin-2-ylmethyl-acetamide;

2-[(2-Chloro-5-dimethylamino-phenyl)-(3,4-dimethoxy-benzenesulfonyl)-amino]-N-ethyl-N-(5-methyl-isoxazol-3-ylmethyl)-acetamide;

2-[(2-Chloro-5-dimethylamino-phenyl)-(3,4-dimethoxy-benzenesulfonyl)-amino]-N,N-diethyl-acetamide;

2-[(2-Cyano-5-dimethylamino-phenyl)-(3,4-dimethoxy-benzenesulfonyl)-amino]-N,N-diethyl-acetamide;

2-[(2-Chloro-5-dimethylamino-phenyl)-(3,4-dimethoxy-benzenesulfonyl)-amino]-N-ethyl-N-(6-methoxy-pyridin-2-ylmethyl)-acetamide; and 2-[(3,4-dimethoxy-benzenesulfonyl)-(5-dimethylamino-2-fluoro-phenyl)-amino]-N-ethyl-N-pyridin-2-ylmethyl-acetamide.

11. The pharmaceutical composition according to claim 9, wherein said compound is 2-[(2-Chloro-5-dimethylamino-phenyl)-(3,4-dimethoxy-benzenesulfonyl)-amino]-N-ethyl-N-(1,5-dimethyl-1H-pyrazol-3-ylmethyl)-acetamide.

12. The pharmaceutical composition according to claim 9, wherein said compound is 2-[(2-Chloro-5-dimethylamino-phenyl)-(3,4-dimethoxy-benzenesulfonyl)-amino]-N-ethyl-N-(6-methyl-pyrazin-2-ylmethyl)-thioacetamide.

* * * * *